(12) United States Patent
Ogasawara et al.

(10) Patent No.: US 7,468,212 B2
(45) Date of Patent: Dec. 23, 2008

(54) ORGANIC ELECTROLUMINESCENT DEVICE

(75) Inventors: Jun Ogasawara, Minami-ashigara (JP); Tatsuya Igarashi, Minami-ashigara (JP); Satoshi Sano, Minami-ashigara (JP)

(73) Assignee: Fujifilm Corporation, Tokyo (JP)

( * ) Notice: Subject to any disclaimer, the term of this patent is extended or adjusted under 35 U.S.C. 154(b) by 464 days.

(21) Appl. No.: 10/990,463

(22) Filed: Nov. 18, 2004

(65) Prior Publication Data

US 2005/0112407 A1  May 26, 2005

(30) Foreign Application Priority Data

Nov. 21, 2003  (JP) ............................. 2003-393050
Oct. 28, 2004  (JP) ............................. 2004-314729

(51) Int. Cl.
*H01L 51/54* (2006.01)

(52) U.S. Cl. .................. 428/690; 428/917; 313/504; 313/506; 257/40; 257/E51.049

(58) Field of Classification Search ............... None
See application file for complete search history.

(56) References Cited

U.S. PATENT DOCUMENTS

| 5,484,922 | A  | * | 1/1996 | Moore et al. | .................. 546/7 |
| 6,416,887 | B1 | * | 7/2002 | Tokito et al. | ................ 428/690 |
| 2001/0006741 | A1 | * | 7/2001 | Ishikawa et al. | ............ 428/690 |
| 2001/0008711 | A1 | * | 7/2001 | Igarashi | ..................... 428/690 |
| 2004/0137268 | A1 | * | 7/2004 | Igarashi et al. | .............. 428/690 |

FOREIGN PATENT DOCUMENTS

JP  2001-167884 A  6/2001
WO  WO 2004/062324 A1 *  7/2004

\* cited by examiner

*Primary Examiner*—Marie R. Yamnitzky
(74) *Attorney, Agent, or Firm*—Birch, Stewart, Kolasch & Birch, LLP

(57) ABSTRACT

An organic electroluminescent device, which has, between a pair of electrodes, at least one organic layer including a light-emitting layer, in which the organic layer contains a specific tetraphenylene compound, and in which the light-emitting layer contains a phosphorescent material; and a specific tetraphenylene compound that can be used in the device.

15 Claims, No Drawings

ORGANIC ELECTROLUMINESCENT DEVICE

FIELD OF THE INVENTION

The present invention relates to an organic electroluminescent device capable of converting electric energy to light, to emit light.

BACKGROUND OF THE INVENTION

In these days, research and development are being vigorously made on various display devices. Especially, organic electroluminescent (EL) devices have been noted as promising display devices since they can emit light with a high luminance at a low voltage. Conventional condensed-ring aromatic compounds used in EL devices are chemically stable but low in the lowest triplet excitation energy level ($T_1$). It is therefore desired that organic electroluminescence devices using triplet luminescence be further improved.

As described above, condensed-ring aromatic compounds are generally low in the $T_1$ energy level; therefore, the compounds are disadvantageous in efficiency for transferring energy to dopants. To improve the luminous efficiency, it has been desired to develop aromatic hydrocarbon materials having a higher $T_1$ energy level. For example, JP-A-2001-167884 ("JP-A" means unexamined published Japanese patent application) discloses an organic electroluminescence device using tetraphenylene, but the device lacks satisfactory luminous efficiency.

SUMMARY OF THE INVENTION

The present invention relates to an organic electroluminescent device, which has, between a pair of electrodes, at least one organic layer including a light-emitting layer, wherein the organic layer contains at least one compound represented by the following formula (1), and wherein the light-emitting layer contains a phosphorescent material:

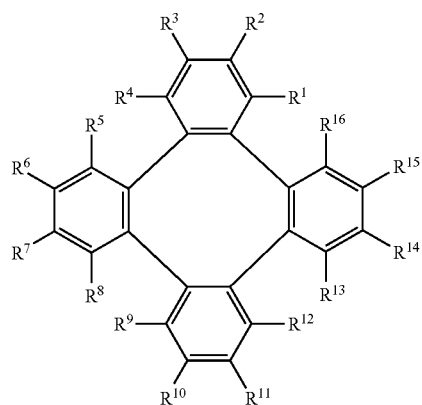

Formula (1)

wherein, in formula (1), $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ each represent a hydrogen atom or a substituent.

Further, the present invention relates to an organic electroluminescent device, which has, between a pair of electrodes, at least one organic layer including a light-emitting layer, wherein the organic layer contains at least one compound represented by the following formula (2):

$$L\text{-}(T)_n \qquad \text{Formula (2)}$$

wherein, in formula (2), L represents a single bond, or a divalent or higher valent linking group; T represents a group obtained by removing an atom from any one of $R^1$ to $R^{16}$ in the structure represented by the above formula (1), or a group obtained by removing any one of $R^1$ to $R^{16}$ from the compound represented by the above formula (1); T's are independently form each other, which may be the same or different from each other; and n represents an integer of 2 or more.

Further, the present invention relates to an organic electroluminescent device, which has, between a pair of electrodes, at least one organic layer including a light-emitting layer, wherein the organic electroluminescent device contains at least one compound represented by the following formula (1A):

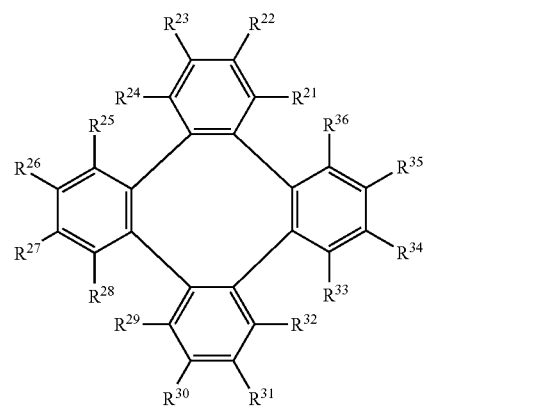

Formula (1A)

wherein, in formula (1A), $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, and $R^{36}$ each represent a hydrogen atom or a substituent; and at least one of $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, and $R^{36}$ is a group having a Hammett $\sigma_p$ value of 0.05 or more.

Further, the present invention relates to an organic electroluminescent device, which has, between a pair of electrodes, at least one organic layer including a light-emitting layer, wherein the organic electroluminescent device contains at least one compound represented by the following formula (1B):

Formula (1B)

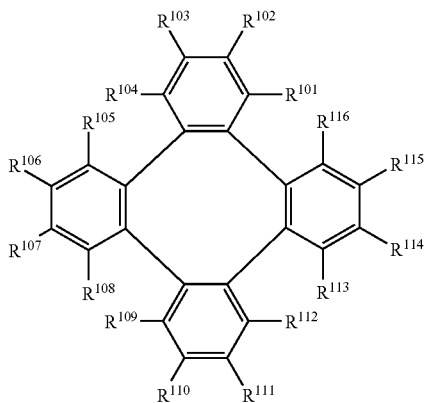

wherein, in formula (1B), $R^{101}$, $R^{102}$, $R^{103}$, $R^{104}$, $R^{105}$, $R^{106}$, $R^{107}$, $R^{108}$, $R^{109}$, $R^{110}$, $R^{111}$, $R^{112}$, $R^{113}$, $R^{114}$, $R^{115}$ and $R^{116}$, which may be the same or different from each other, each represent a substituent; and at least one of these substituents represents a substituted or unsubstituted aryl group.

Further, the present invention relates to a compound represented by the above formula (2).

Other and further features and advantages of the invention will appear more fully from the following description.

DETAILED DESCRIPTION OF THE INVENTION

According to the present invention, there are provided the following means:

(1) An organic electroluminescent device, having, between a pair of electrodes, at least one organic layer including a light-emitting layer (which may also be referred to as a luminous layer), wherein the organic layer contains at least one compound represented by formula (1), and wherein the light-emitting layer contains a-phosphorescent material (which may also be referred to as a triplet light-emitting material):

Formula (1)

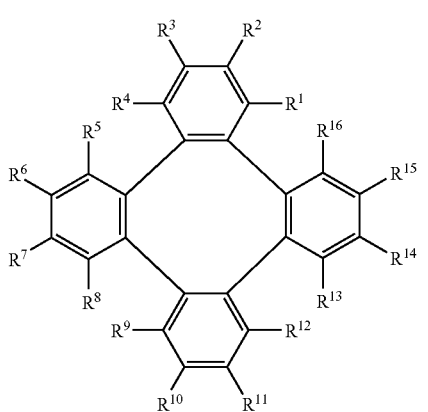

wherein, in formula (1), $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ each represent a hydrogen atom or a substituent;

(2) An organic electroluminescent device, having, between a pair of electrodes, at least one organic layer including a light-emitting layer, wherein the organic layer contains at least one compound represented by formula (2):

$$L\text{-}(T)_n$$ Formula (2)

wherein, in formula (2), L represents a single bond, or a divalent or higher valent linking group; T represents a group obtained by removing an atom, such as a hydrogen atom, from any one of $R^1$ to $R^{16}$ in the structure represented by formula (1), or a group obtained by removing any one of $R^1$ to $R^{16}$ from the compound represented by formula (1); T's are independently form each other, which may be the same or different from each other; and n represents an integer of 2 or more;

Formula (1)

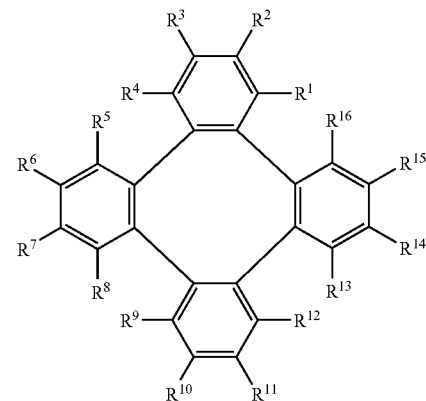

wherein, in formula (1), $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ each represent a hydrogen atom or a substituent;

(3) An organic electroluminescent device, having, between a pair of electrodes, at least one organic layer including a light-emitting layer, wherein the organic electroluminescent device contains at least one compound represented by formula (1A):

Formula (1A)

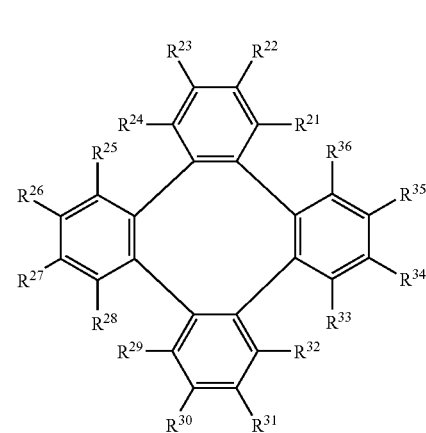

wherein, in formula (1A), $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, and $R^{36}$ each represent a hydrogen atom or a substituent; and at least one of $R^{21}$, $R^{22}$, $R^{23}, R^{24}, R^{25}, R^{26}, R^{27}, R^{28}, R^{29}, R^{30}, R^{31}, R^{32}, R^{33}, R^{34}, R^{35}$, and $R^{36}$ is a group having a Hammett $\sigma_P$ value of 0.05 or more;

(4) An organic electroluminescent device, having, between a pair of electrodes, at least one organic layer including a light-emitting layer, wherein the organic electroluminescent device contains at least one compound represented by formula (1B):

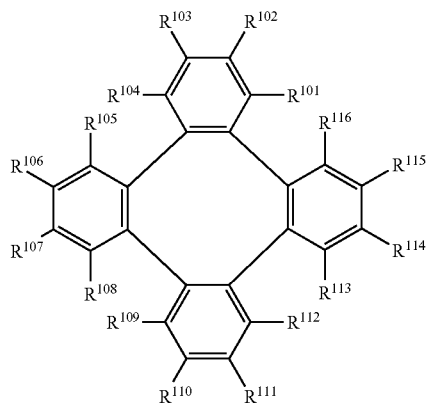

Formula (1B)

wherein, in formula (1B), $R^{101}$, $R^{102}$, $R^{103}$, $R^{104}$, $R^{105}$, $R^{106}$, $R^{107}$, $R^{108}$, $R^{109}$, $R^{110}$, $R^{111}$, $R^{112}$, $R^{113}$, $R^{114}$, $R^{115}$, and $R^{116}$, which may be the same or different from each other, each represent a substituent; and at least one of these substituents represents a substituted or unsubstituted aryl group;

(5) The organic electroluminescent device according to the above item (4), wherein the compound represented by formula (1B) is a compound represented by formula (1C):

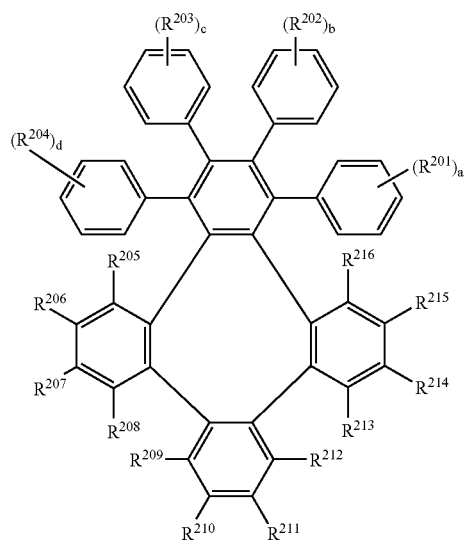

Formula (1C)

wherein, in formula (1C), $R^{201}$, $R^{202}$, $R^{203}$, $R^{204}$, $R^{205}$, $R^{206}$, $R^{207}$, $R^{208}$, $R^{209}$, $R^{210}$, $R^{211}$, $R^{212}$, $R^{213}$, $R^{214}$, $R^{215}$, and $R^{216}$, which may be the same or different from each other, each represent a substituent; and a, b, c, and d each independently represent an integer of from 0 to 5;

(6) The organic electroluminescent device according to any one of the above items (1) to (5), wherein the compound represented by formula (1), (2), (1A), (1B) or (1C) is contained in the light-emitting layer;

(7) The organic electroluminescent device according to any one of the above items (1) to (6), wherein the light-emitting layer contains an electron-injecting/transporting compound;

(8) The organic electroluminescent device according to the above item (7), wherein the electron-injecting/transporting compound is a metal complex;

(9) The organic electroluminescent device according to the above item (7) or (8), wherein the electron-injecting/transporting compound is a heterocyclic compound containing at least two nitrogen atoms;

(10) A compound represented by formula (2):

$$L\text{-}(T)_n \qquad \text{Formula (2)}$$

wherein, in formula (2), L represents a single bond, or a divalent or higher valent linking group; T represents a group obtained by removing an atom from any one of $R^1$ to $R^{16}$ in the structure represented by formula (1), or a group obtained by removing any one of $R^1$ to $R^{16}$ from the compound represented by formula (1); T's are independently form each other, which may be the same or different from each other; and n represents an integer of 2 or more;

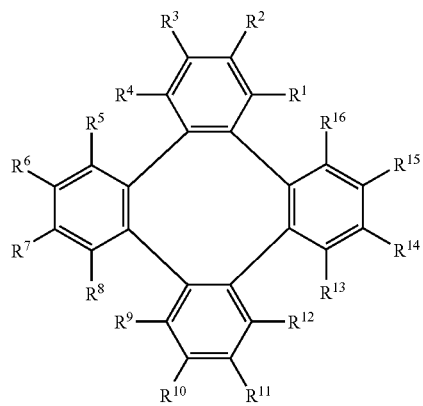

Formula (1)

wherein, in formula (1), $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ each represent a hydrogen atom or a substituent.

The inventors, having eagerly conducted investigations to solve the above-mentioned technical problems in the conventional technique, have found that when a tetraphenylene compound is used together with a phosphorescent material in an electroluminescent device, and, in particular, when as the tetraphenylene compound, a multimer (or polymer) thereof, such as a dimer thereof, is used, the resultant organic light-emitting layer exhibits a high $T_1$ energy level. The inventors have also found that, when this organic light-emitting layer is used in a luminescent device, the resultant device can have a high luminous efficiency and exhibit excellent driving durability (longevity). The present invention has been attained based on these findings.

The present invention relates to an organic electroluminescence device, which comprises, between a pair of electrodes, at least one organic layer (organic-compound layer) that includes a light-emitting layer (luminous layer), and which comprises at least one compound represented by the above formula (1), as well as preferably at least one luminous material, in the organic layer, and which comprises a phosphorescent material.

Luminescence from a material in a triplet excitation state has the same meaning as phosphorescence. Herein (in the specification and claims), a material which emits phosphorescence is referred to as a "phosphorescent material". The phosphorescent material is not particularly limited, but is preferably a transition metal complex. The center metal of the transition metal complex is not particularly limited, but is preferably iridium, platinum, rhenium, or ruthenium, more preferably iridium or platinum, even more preferably iridium.

The transition metal complex is preferably an orthometalated complex. The orthometalated complex referred to herein is a generic designation of compounds described, for example, in "Yuki Kinzoku Kagaku, Kiso to Oyo" ("Organometal Chemistry, Fundamentals and Applications"), by Akio Yamamoto, SHOKABO PUBLISHING Co., Ltd., 1982, pp. 150 and 232; and "Photochemistry and Photophysics of Coordination Compounds" by H. Yersin, Springer-Verlag, 1987, pp. 71-77 and pp. 135-146.

The phosphorescent material that can be used in the present invention is preferably a material having a phosphorescence quantum yield of 70% or more at 20° C., more preferably a material having a phosphorescence quantum yield of 80% or more at 20° C., even more preferably a material having a phosphorescence quantum yield of 85% or more at 20° C. If the phosphorescence quantum yield is too low, the luminous efficiency of the device lowers.

In the luminescent device (light-emitting device) of the present invention, it is preferred to use a layer containing a compound having an ionization potential of 5.9 eV or more (more preferably 6.0 eV or more) between the cathode and the light-emitting layer, and it is more preferred to use an electron transporting layer of 5.9 eV or more in ionization potential.

The luminescent device of the present invention preferably has a light emission spectrum half value width of 100 nm or less, more preferably 90 nm or less, further preferably 80 nm or less, and particularly preferably 70 nm or less, from the viewpoint of the color purity.

The luminescent device of the present invention means to include those in which a luminous material different from a phosphorescent material is excited by exciton energy of the phosphorescent material so that this luminous material substantially emits light.

Descriptions on the compound represented by formula (1) are given below. $R^1$, $R^2$, $R^3$, $R^4$, $R^5$, $R^6$, $R^7$, $R^{7'}$, $R^8$, $R^9$, $R^{10}$, $R^{11}$, $R^{12}$, $R^{13}$, $R^{14}$, $R^{15}$, and $R^{16}$ in formula (1) each represent a hydrogen atom or a substituent. Examples of the substituent include an alkyl group (having preferably 1 to 30, more preferably 1 to 20, particularly preferably 1 to 10 carbon atoms, e.g. methyl, ethyl, iso-propyl, tert-butyl, n-octyl, n-decyl, n-hexadecyl, cyclopropyl, cyclopentyl, and cyclohexyl), an alkenyl group (having preferably 2 to 30, more preferably 2 to 20, particularly preferably 2 to 10 carbon atoms, e.g. vinyl, allyl, 2-butenyl, and 3-pentenyl), an alkynyl group (having preferably 2 to 30, more preferably 2 to 20, particularly preferably 2 to 10 carbon atoms, e.g. propargyl, and 3-pentynyl), an aryl group (having preferably 6 to 30, more preferably 6 to 20, particularly preferably 6 to 12 carbon atoms, e.g. phenyl, p-methylphenyl, naphthyl, and anthranyl), an amino group (having preferably 0 to 30, more preferably 0 to 20, particularly preferably 0 to 10 carbon atoms, e.g. amino, methylamino, dimethylamino, diethylamino, dibenzylamino, diphenylamino, and ditolylamino), an alkoxy group (having preferably 1 to 30, more preferably 1 to 20, particularly preferably 1 to 10 carbon atoms, e.g. methoxy, ethoxy, butoxy, and 2-ethylhexyloxy), an aryloxy group (having preferably 6 to 30, more preferably 6 to 20, particularly preferably 6 to 12 carbon atoms, e.g. phenyloxy, 1-naphthyloxy, and 2-naphthyloxy), a heteroaryl oxy group (having preferably 1 to 30, more preferably 1 to 20, particularly preferably 1 to 12 carbon atoms, e.g. pyridyloxy, pyrazyloxy, pyrimidyloxy, and quinolyloxy), an acyl group (having preferably 1 to 30, more preferably 1 to 20, particularly preferably 1 to 12 carbon atoms, e.g. acetyl, benzoyl, formyl, and pivaloyl), an alkoxycarbonyl group (having preferably 2 to 30, more preferably 2 to 20, particularly preferably 2 to 12 carbon atoms, e.g. methoxycarbonyl, and ethoxycarbonyl), an aryloxycarbonyl group (having preferably 7 to 30, more preferably 7 to 20, particularly preferably 7 to 12 carbon atoms, e.g. phenyloxycarbonyl), an acyloxy group (having preferably 2 to 30, more preferably 2 to 20, particularly preferably 2 to 10 carbon atoms, e.g. acetoxy, and benzoyloxy), an acylamino group (having preferably 2 to 30, more preferably 2 to 20, particularly preferably 2 to 10 carbon atoms, e.g. acetylamino, and benzoylamino), an alkoxycarbonylamino group (having preferably 2 to 30, more preferably 2 to 20, particularly preferably 2 to 12 carbon atoms, e.g. methoxycarbonylamino), an aryloxycarbonylamino group (having preferably 7 to 30, more preferably 7 to 20, particularly preferably 7 to 12 carbon atoms, e.g. phenyloxycarbonylamino), a sulfonylamino group (having preferably 1 to 30, more preferably 1 to 20, particularly preferably 1 to 12 carbon atoms, e.g. methanesulfonylamino, and benzenesulfonylamino), a sulfamoyl group (having preferably 0 to 30, more preferably 0 to 20, particularly preferably 0 to 12 carbon atoms, e.g. sulfamoyl, methylsulfamoyl, dimethylsulfamoyl, and phenylsulfamoyl), a carbamoyl group (having preferably 1 to 30, more preferably 1 to 20, particularly preferably 1 to 12 carbon atoms, e.g. carbamoyl, methylcarbamoyl, diethylcarbamoyl, and phenylcarbamoyl), an alkylthio group (having preferably 1 to 30, more preferably 1 to 20, particularly preferably 1 to 12 carbon atoms, e.g. methylthio, and ethylthio), an arylthio group (having preferably 6 to 30, more preferably 6 to 20, particularly preferably 6 to 12 carbon atoms, e.g. phenylthio), a heteroaryl thio group (having preferably 1 to 30, more preferably 1 to 20, particularly preferably 1 to 12 carbon atoms, e.g. pyridylthio, 2-benzimidazolylthio, 2-benzoxazolylthio, and 2-benzothiazolylthio), a sulfonyl group (having preferably 1 to 30, more preferably 1 to 20, particularly preferably 1 to 12 carbon atoms, e.g. mesyl, and tosyl), a sulfinyl group (having preferably 1 to 30, more preferably-1 to 20, particularly preferably 1 to 12 carbon atoms, e.g. methanesulfinyl, and benzenesulfinyl), a ureido group (having preferably 1 to 30, more preferably 1 to 20, particularly preferably 1 to 12 carbon atoms, e.g. ureido, methylureido, and phenylureido), a phosphoric acid amido group (having preferably 1 to 30, more preferably 1 to 20, particularly preferably 1 to 12 carbon atoms, e.g. diethylphosphoric acid amido, and phenylphosphoric acid amido), a hydroxyl group, a mercapto group, a halogen atom (e.g., a fluorine atom, a chlorine atom, a bromine atom, or an iodine atom), a cyano group, a sulfo group, a carboxyl group, a nitro group, a hydroxamic acid group, a sulfino group, a hydrazino group, an imino group, a heterocyclic group (having preferably 1 to 30, more preferably 1 to 12 carbon atoms, with a hetero atom, for example, of a nitrogen atom, an oxygen atom, or a sulfur atom, specific examples include imidazolyl, pyridyl, quinolyl, furyl, thienyl, piperidyl, morpholino, benzoxazolyl, benzimidazolyl, benzothiazolyl, carbazolyl, and azepinyl), and a silyl group (having preferably 3 to 40, more preferably 3 to 30, particularly preferably 3 to 24 carbon atoms, e.g. trimethylsilyl, and triphenylsilyl). These substituents may further be substituted by those groups and atoms, or they may bond each other to form a ring.

Examples of the substituent that may be contained in $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ are preferably an alkyl group, an aryl group, and a heteroaryl group; and more preferably an aryl group and a heteroaryl group.

Two or more compounds represented by formula (1) may bond each other, through any of $R^1$ to $R^{16}$ on the skeleton thereof, or by removing an atom of any of $R^1$ to $R^{16}$, such as a hydrogen atom, to form a dimer or a higher multimer. The compounds represented by formula (1) may be low molecular compounds, oligomer compounds, or polymer compounds (having a weight average molecular weight (in terms of polystyrene) of preferably 1,000 to 5,000,000, more preferably 2,000 to 1,000,000, still more preferably 3,000 to 100,000). When the compounds are polymer compounds, the tetraphenylene structure may be contained to constitute a polymer main chain, and/or contained in a polymer side chain. In the case of the polymer compounds, they may be homopolymer compounds or copolymer compounds. The compounds according to the present invention are preferably low molecular compounds.

The $T_1$ level (the energy level of the lowest triplet excitation state) of the compound represented by formula (1) is preferably from 45 kcal/mol (188.3 kJ/mol) to 85 kcal/mol (355.6 kJ/mol), more preferably from 55 kcal/mol (251.0 kJ/mol) to 85 kcal/mol (355.6 kJ/mol), even more preferably from 60 kcal/mol (272.0 kJ/mol) to 85 kcal/mol (355.6 kJ/mol). The preferable $T_1$ level of the compound represented by formula (1A), (1B) or (1C) is the same as that mentioned in the above for the compound of the formula (1).

The $T_1$ level of the compound represented by formula (2) is preferably from 55 kcal/mol (251.0 kJ/mol) to 85 kcal/mol (355.6 kJ/mol), more preferably from 60 kcal/mol (272.0 kJ/mol) to 85 kcal/mol (355.6 kJ/mol).

The following describes the compound represented by formula (2). L represents a single bond, or a divalent or higher-valent linking group (in other words, a linking group whose valences are divalent or higher valent). The linking group represented by L is preferably a single bond, or a linking group formed, for example, from C, N, O, S, Si, or Ge; more preferably a single bond, a divalent or higher-valent aromatic ring, a divalent or higher-valent aromatic heteroring, a carbon atom, a nitrogen atom, or a silicon atom; and most preferably a single bond, a divalent or higher-valent benzene ring, a divalent or higher-valent naphthalene ring, a divalent or higher-valent biphenyl ring, a divalent or higher-valent terphenyl ring, a divalent or higher-valent triphenylene ring, a divalent or higher-valent phenanthrene ring, a divalent or higher-valent triazole ring, a divalent or higher-valent pyridine ring, a divalent or higher-valent pyrimidine ring, a carbon atom, a nitrogen atom, or a silicon atom. The compound represented by formula (2) corresponds to a dimer or a higher multimer, in which two or more of the compounds represented by formula (1) are bonded to each other through each group obtained by removing an atom, such as a hydrogen atom, from any one of $R^1$ to $R^{16}$ of each compound of the formula (1), or are bonded to each other by removing any one of $R^1$ to $R^{16}$ of each compound.

The linking group represented by L may have a substituent(s). The substituent has the same meaning as those described on $R^1$ to $R^{16}$. The substituent is preferably an alkyl group, an aryl group, or a heteroaryl group, more preferably an aryl group, or a heteroaryl group.

Specific examples of the linking group represented by L include a single bond, and groups as illustrated below. However, L in the present invention is not limited to these. In each of the linking groups illustrated below, it is allowable to bond, to all of its free bonding hands, tetraphenylene groups derived from the compound represented by formula (1). However, the linking groups are not limited to this embodiment. It is sufficient that the tetraphenylene groups are bonded to at least two of the free bonding hands. In this case, one or more hydrogen atoms or ordinary substituents (e.g. the group or atom represented by any of $R^1$ to $R^{16}$) may be bonded to the bonding hand(s) to which no tetraphenylene group is bonded.

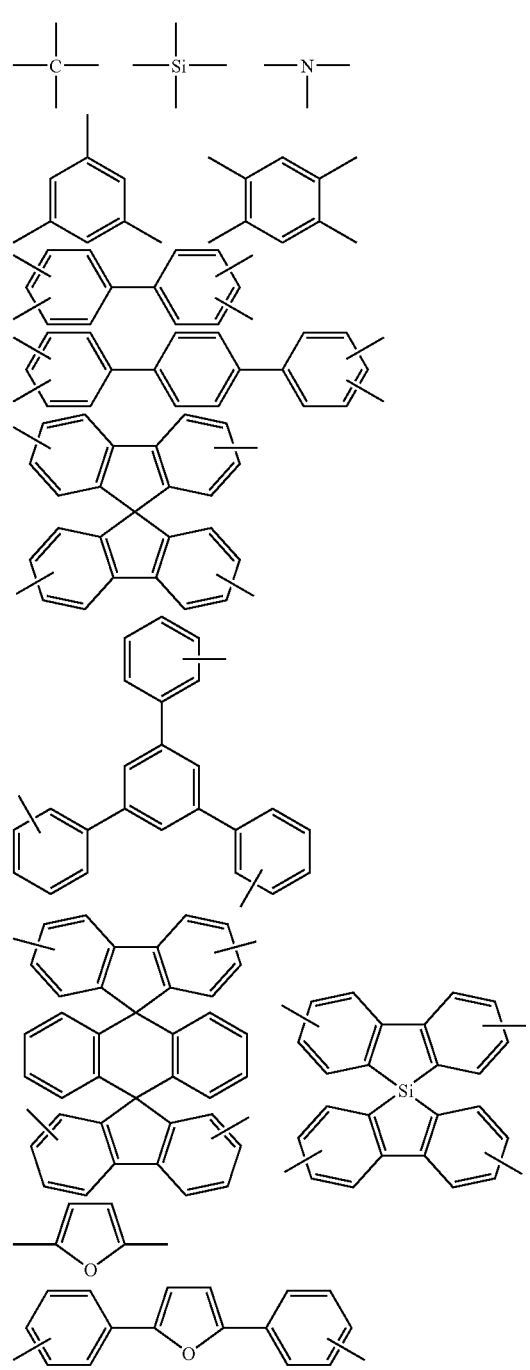

-continued
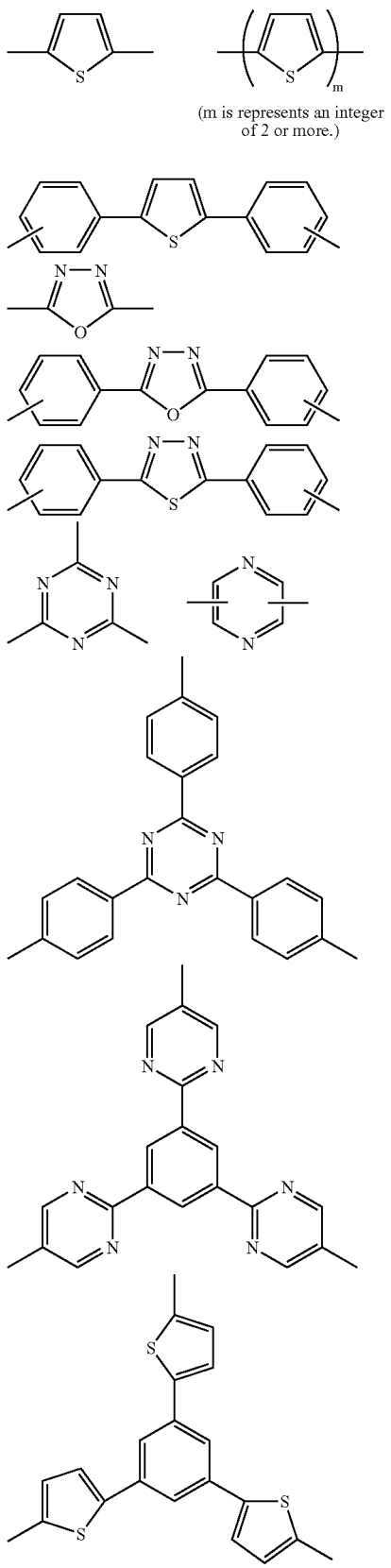
-continued
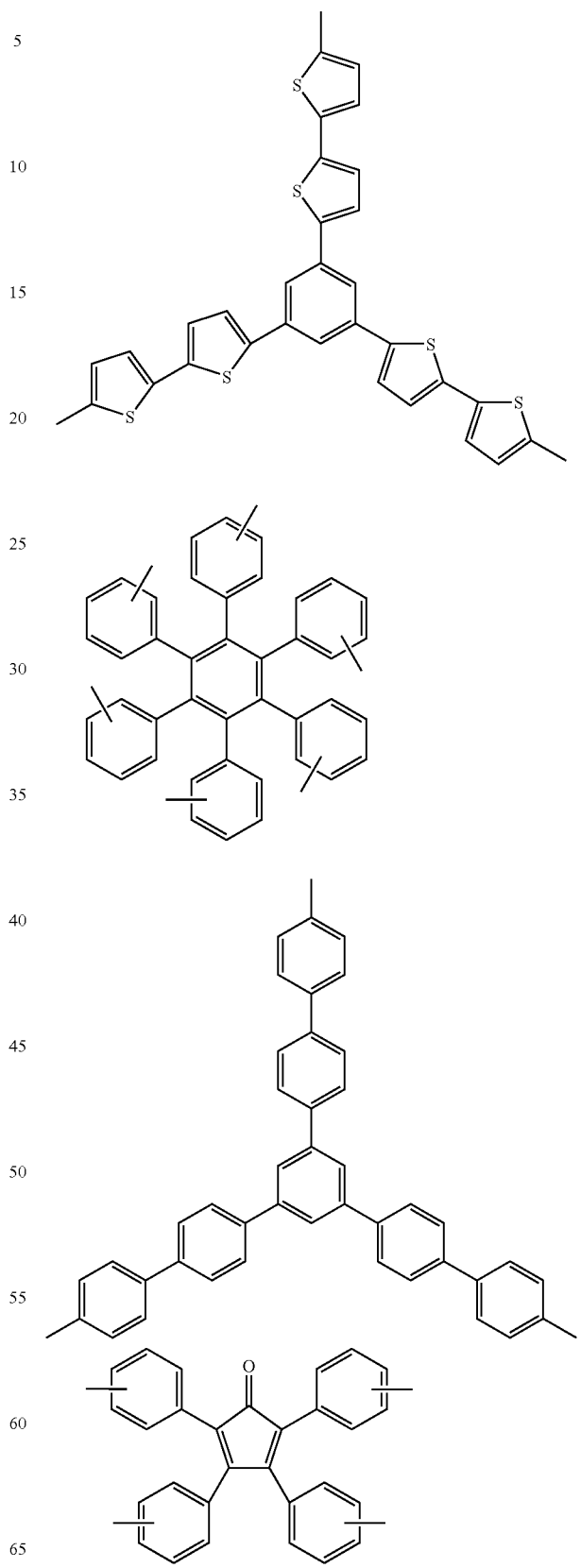

-continued

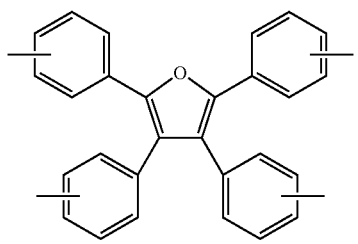

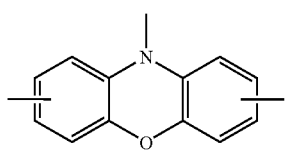

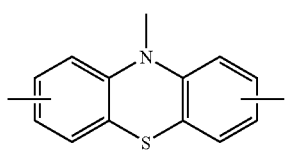

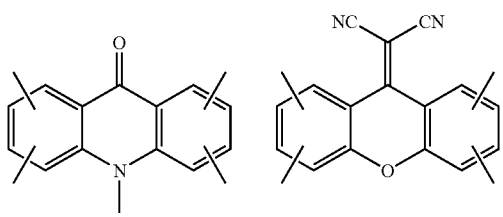

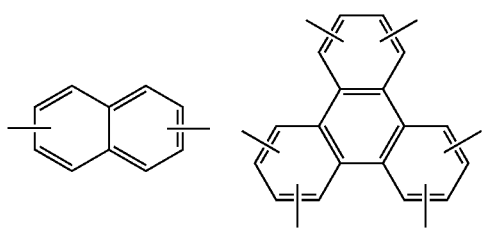

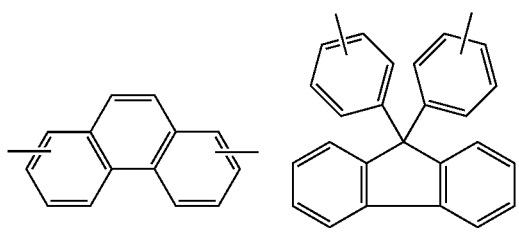

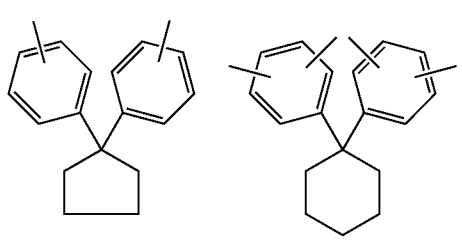

-continued

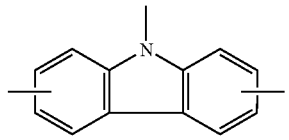

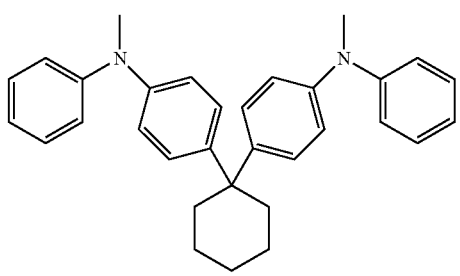

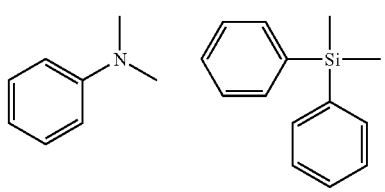

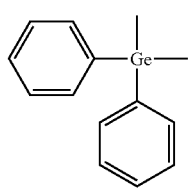

In formula (2), n represents an integer of 2 or more, and is preferably an integer of 2 to 8, more preferably an integer of 2 to 4.

The ratio of the compound represented by formula (1) or (2) to the phosphorescent material varies according to the structure of the former, the $T_1$ level of the latter, and other conditions. The ratio of said compound to said material by mass is preferably from 50/50 to 99.9/0.1, more preferably from 80/20 to 99/1.

In the organic electroluminescence device of the present invention, when the organic layer contains the compound represented by formula (2), the durability of the resultant device can be improved. The reason for this has not yet been made clear, but can be presumed, for example, as follows:

(1) Since the number of charge transporting sites is large, the carrier transporting ability of the compound is improved, thereby the efficiency of the resultant luminescence device is improved. As a result, the durability thereof is also improved;

(2) The amorphousness of the molecule is improved or the Tg thereof is improved, thereby to suppress the crystallization in the device or interface-mixing therein. As a result, the durability is improved.

The present invention further relates to an organic electroluminescent device, which has, between a pair of electrodes, at least one organic layer including a light-emitting layer, in which the organic electroluminescent device contains at least one compound represented by formula (1A), (1B) or (1C):

Formula (1A)

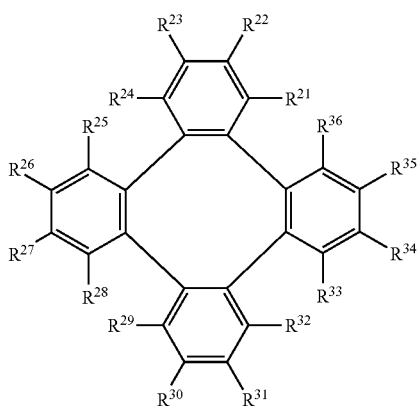

wherein, in formula (1A), $R^{21}$ to $R^{36}$ each are a hydrogen atom or a substituent, and at least one of $R^{21}$ to $R^{36}$ is a group having the Hammett $\sigma_P$ constant of 0.05 or more;

Formula (1B)

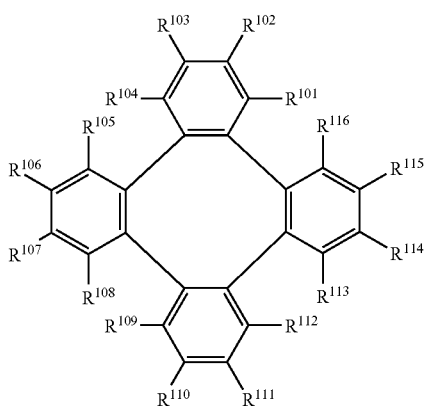

wherein, in formula (1B), $R^{101}$ to $R^{116}$, which may be the same or different, each represent a substituent, and at least one of $R^{101}$ to $R^{116}$ is a substituted or unsubstituted aryl group;

Formula (1C)

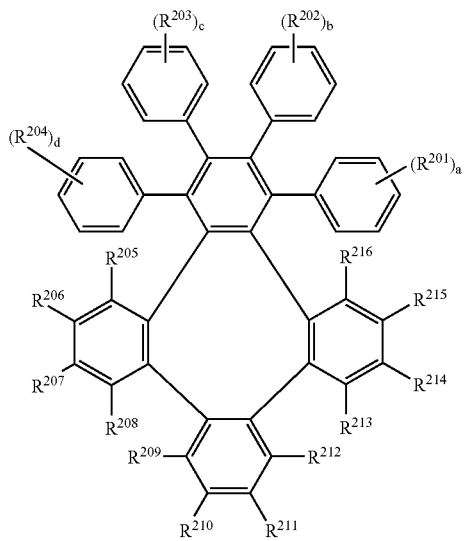

wherein, in formula (1C), $R^{201}$ to $R^{216}$, which may be the same or different, each represent a substituent; and the reference symbols a, b, c, and d each independently represent an integer of from 0 to 5.

In this case, it is preferred that the compound represented by formula (1A), (1B) or (1C) is contained as a host material in the light-emitting layer.

In the case that the compound represented by formula (1A), (1B) or (1C) is contained in the luminescent device of the present invention, the luminous material may be a fluorescence light-emitting compound, which emits light from its singlet excitons, or a phosphorescence light-emitting compound, which emits light from its triplet excitons. The phosphorescence light-emitting (material) compound is preferred.

Examples of the luminous material include various metal complexes, typical examples of which are rare earth complexes, transition metal complexes, metal complexes of pyrromethene and derivatives thereof, metal complexes of 8-quinolinol and derivatives thereof, benzoxazole and derivatives thereof, benzoimidazole and derivatives thereof, benzothiazole and derivative thereof, styrylbenzene and derivatives thereof, polyphenyl and derivatives thereof, diphenylbutadiene and derivatives thereof, tetraphenylbutadiene and derivatives thereof, naphthalimide and derivatives thereof, coumarin and derivatives thereof, condensed aromatic compounds, perynone and derivatives thereof, oxadiazole and derivatives thereof, oxazine and derivatives thereof, aldazine and derivatives thereof, pyrazine (or pyrizine) and derivatives thereof, cyclopentadiene and derivatives thereof, bisstyrylanthracene and derivatives thereof, quinacridon and derivatives thereof, pyrrolopyridine and derivatives thereof, thiadiazolopyridine and derivatives thereof, cyclopentadiene and derivatives thereof, styrylamine and derivatives thereof, diketopyrrolopyrrole and derivatives thereof, aromatic dimethylidene and derivatives thereof; polymer compounds, e.g. polythiophene, polyphenylene, and poly(phenylene vinylene); and organosilicon and derivatives thereof. As the luminous material, preferable are transition metal complexes, rare earth complexes, and metal complexes of pyrromethene and derivatives thereof, condensed aromatic compounds, quinacridon and derivatives thereof, diketopyrrolopyrrole and derivatives thereof. More preferable are transition metal complexes, condensed aromatic compounds.

In the case that the luminous material is a phosphorescence light-emitting material, a preferred scope of the phosphorescence material is the same as the phosphorescence material that can be contained in the device containing the compound represented by formula (1).

The following describes, in detail, the compound of the formula (1A).

Formula (1A)

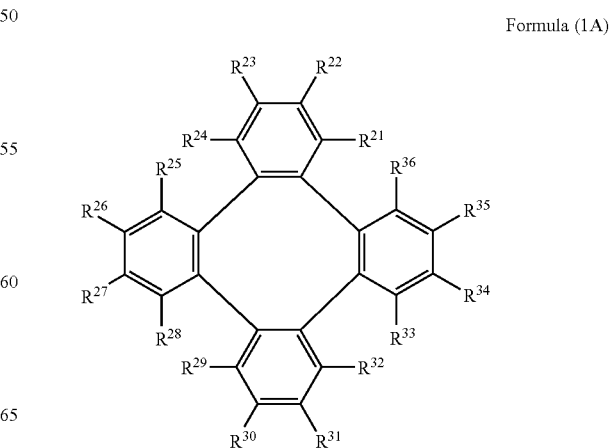

In the formula, $R^{21}$ to $R^{36}$ each are a hydrogen atom or a substituent, and at least one of $R^{21}$ to $R^{36}$ is a group having the Hammett $\sigma_P$ constant of 0.05 or more.

The substituent is selected from, for example, the groups and atoms described on the above $R^1$ to $R^{16}$, and is preferably a group containing a heterocyclic skeleton having 2 or more nitrogen atoms, or a halogen atom, more preferably a group containing a pyridine ring, benzimidazole ring or imidazopyridine ring skeleton, or a fluorine or chlorine atom, even more preferably a group containing a pyridine ring or imidazopyridine ring skeleton, or a fluorine atom.

The compound represented by formula (1) preferably has only one tetraphenylene structure.

The following describes the compound of the formula (1B).

Formula (1B)

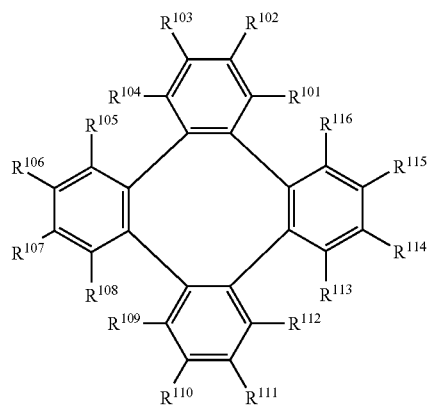

In the formula, $R^{101}$ to $R^{116}$, which may be the same or different from each other, each represent a substituent. The substituent may be the same substituent as described on the above $R^1$ to $R^{16}$. At least one of $R^{101}$ to $R^{116}$ is a substituted or unsubstituted aryl group.

The aryl group is a monocyclic aryl group, or an aryl group having a condensed ring, in which two or more rings are condensed. The number of carbon atoms in the aryl group is preferably from 6 to 30, more preferably from 6 to 20, even particularly preferably from 6 to 12. Examples of the aryl group include phenyl; biphenyl, terphenyl, naphthyl, anthryl, phenanthrenyl, pyrenyl, perylenyl, fluorenyl, ruburenyl, chrysenyl, triphenylenyl, benzanthryl, benzophenanthrenyl, and diphenylanthryl groups.

The aryl group is preferably a phenyl, biphenyl, terphenyl, naphthyl, or anthryl group, more preferably a phenyl, biphenyl or naphthyl group, most preferably a phenyl group.

The following describes the compound of the formula (1C).

Formula (IC)

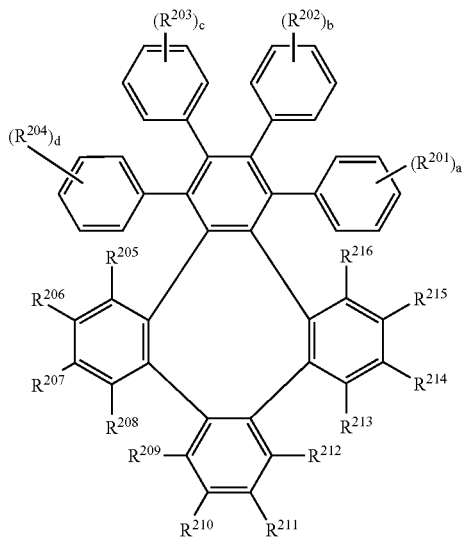

In formula (1c), $R^{201}$ to $R^{216}$ which may be the same or different from each other, each represent a substituent. The substituent may be the same substituent as described on the above $R^1$ to $R^{16}$. $R^{201}$ to $R^{216}$ each independently are preferably an alkyl or aryl group, more preferably a methyl, ethyl, phenyl or biphenyl group, even more preferably a methyl or phenyl group.

The symbols a, b, c and d each independently represent an integer of 0 to 5, and the symbols a, b, c and d each independently are preferably from 0 to 3, more preferably 0 or 1, even more preferably 0.

The following illustrates examples of the compounds represented by formula (1), (2), (1A), (1B) or (1C) according to the present invention. In the present invention, however, the compounds are not limited to these.

(1-1)

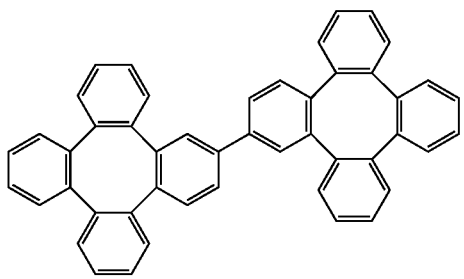

(1-2)

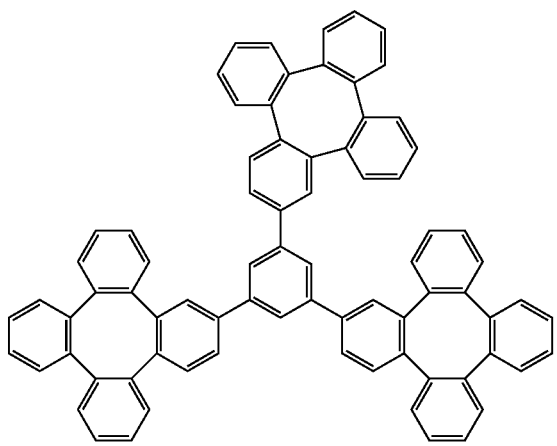

-continued
(1-3)
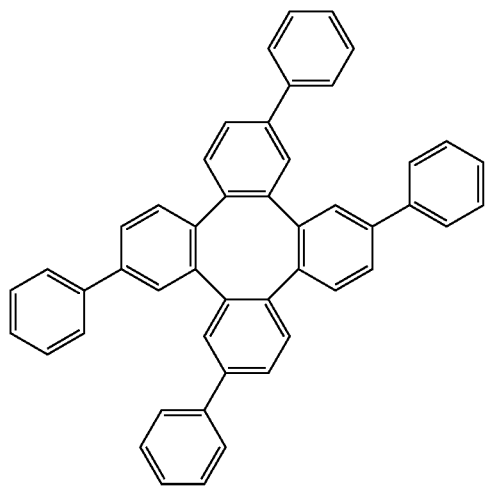
(1-4)
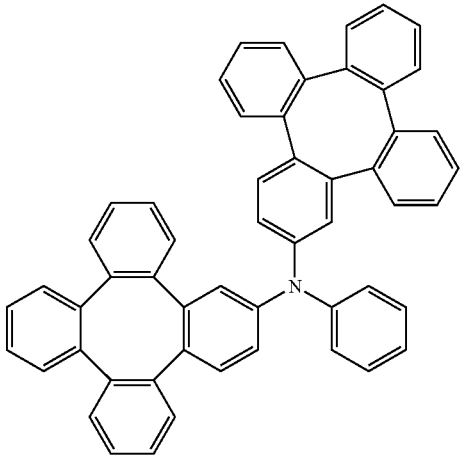
(1-5)
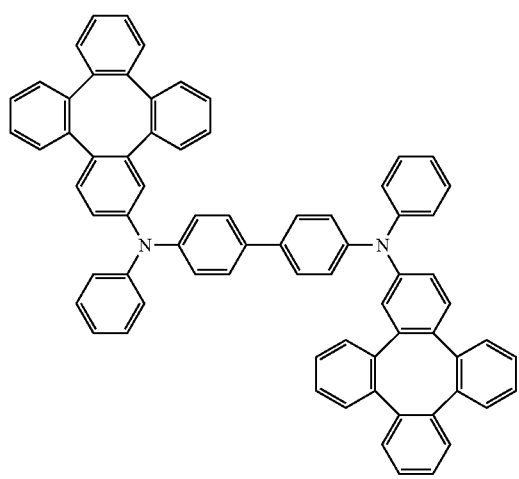
(1-6)
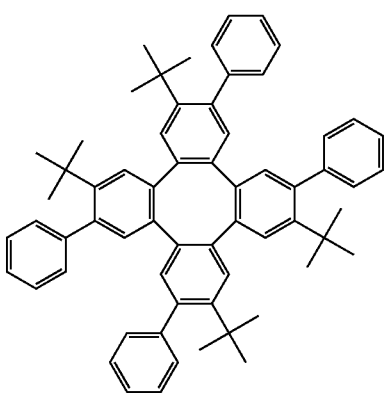
(1-7)
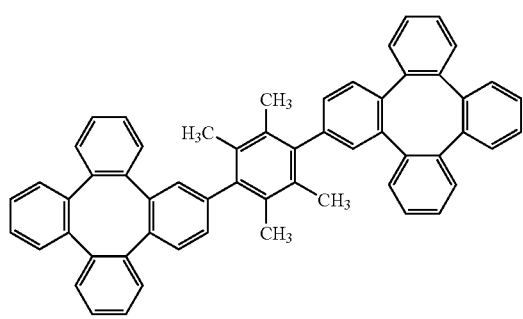
(1-8)
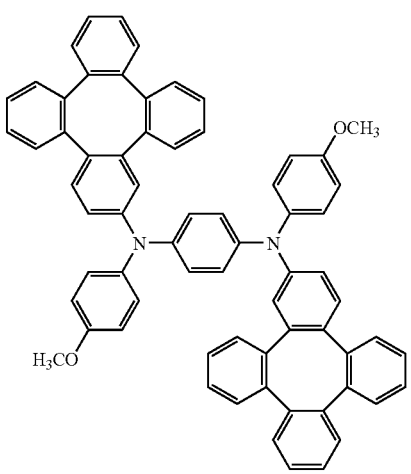

-continued
(1-9)
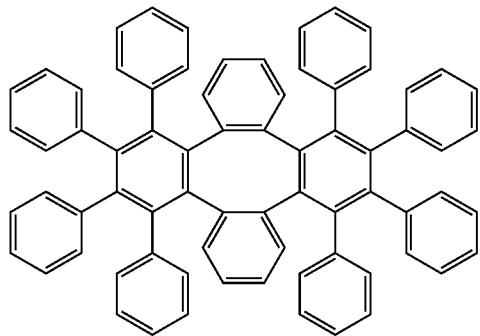
(1-10)
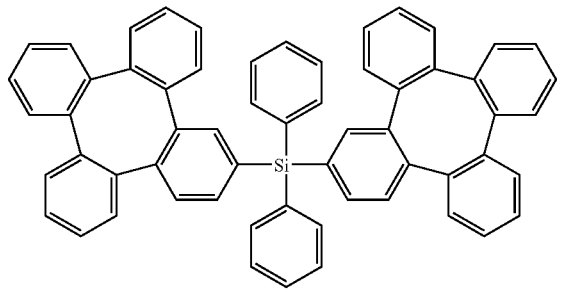
(1-11)
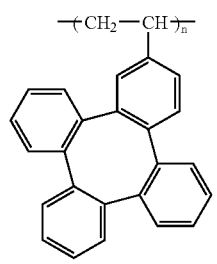
(1-12)
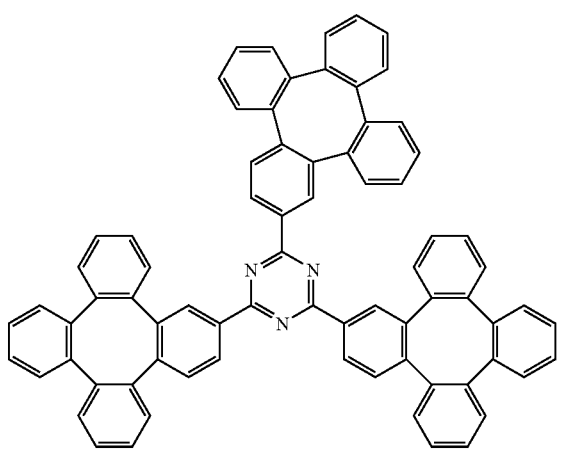
(1-13)
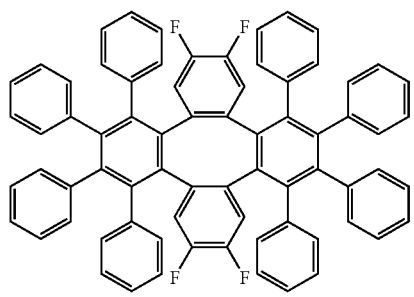
(1-14)
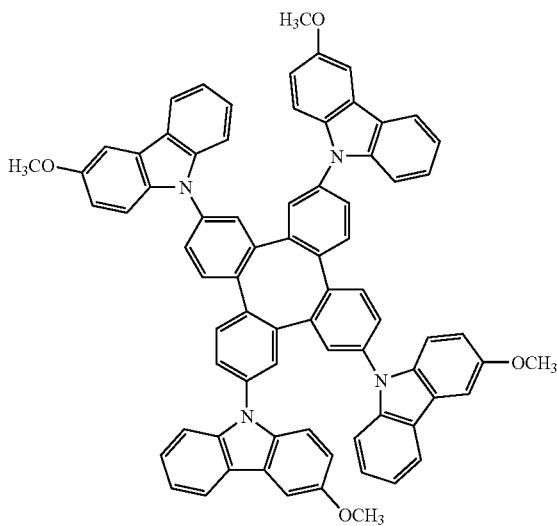

-continued
(1-15)
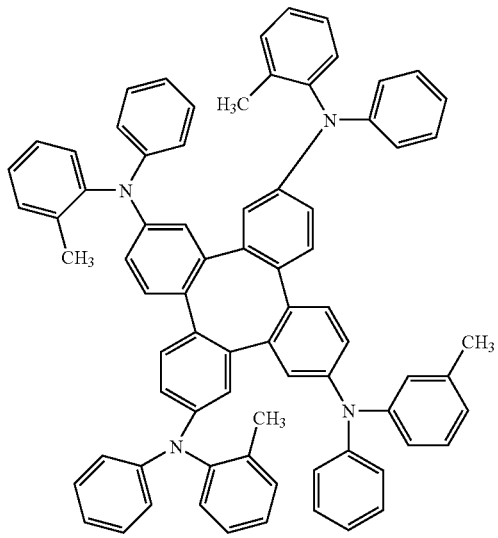
(1-16)
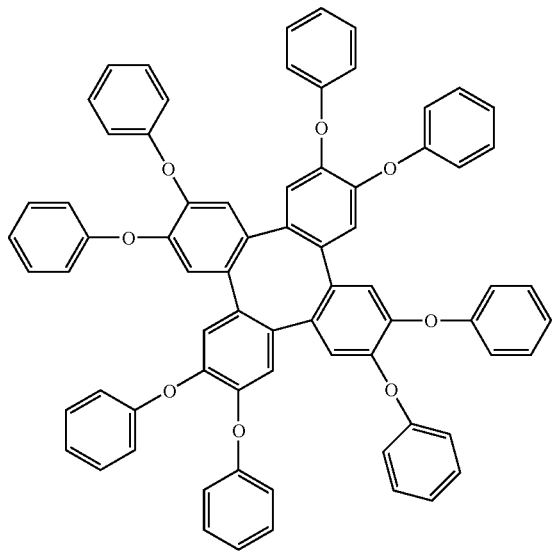
(2-1)
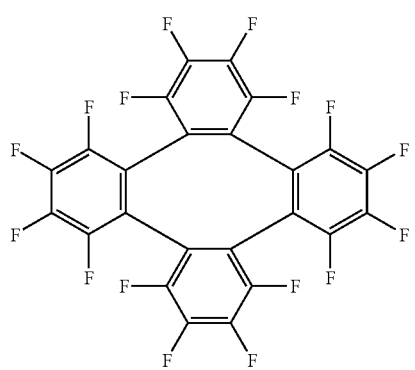
(2-2)
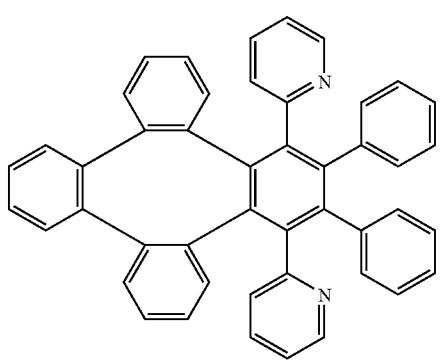
(2-3)
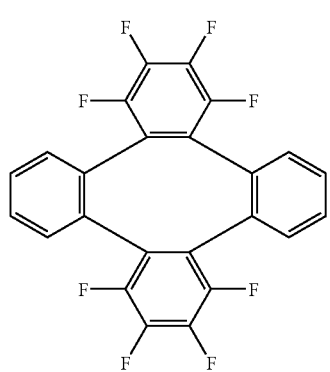
(2-4)
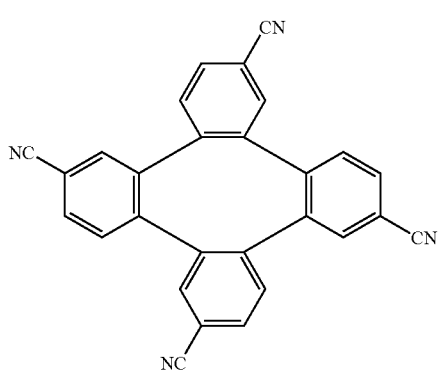

-continued
(2-5)
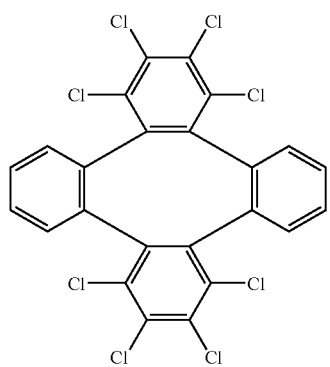
(2-6)
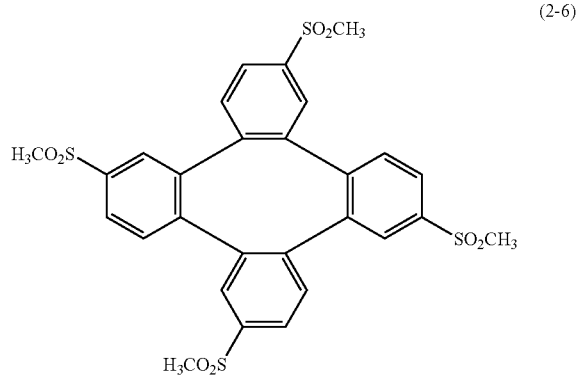
(2-7)
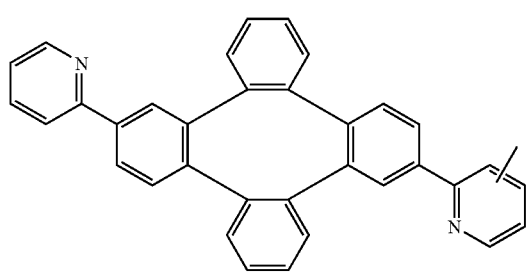
(2-8)
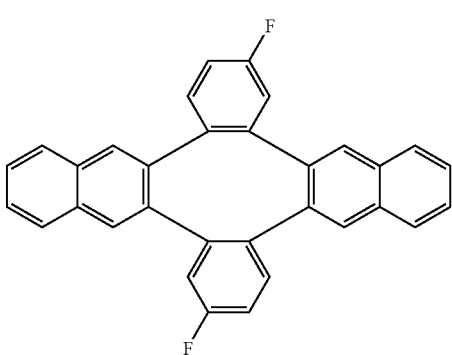
(2-9)
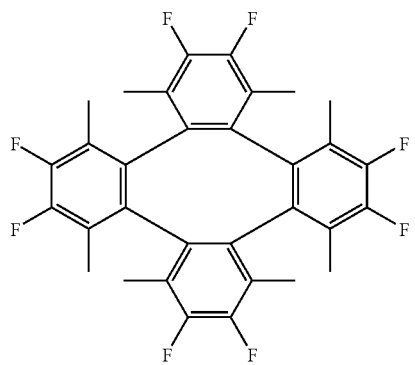
(2-10)
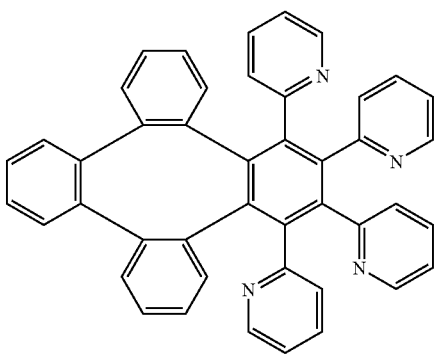
(2-11)
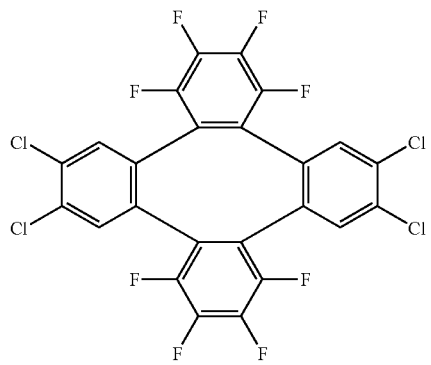
(2-12)
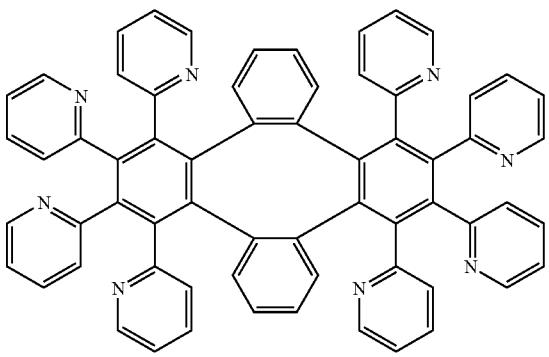

-continued
(2-13)
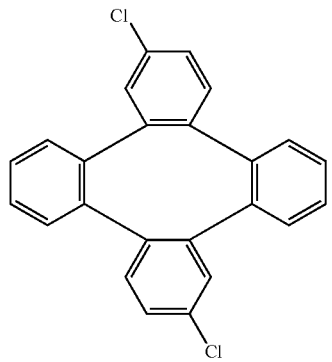
(2-14)
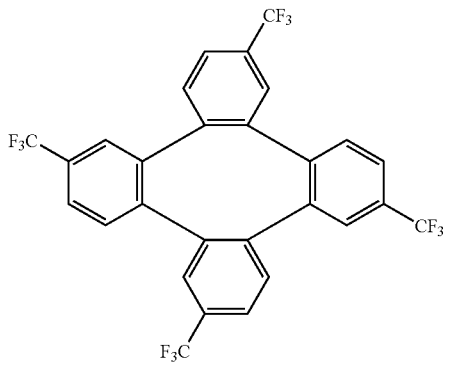
(2-15)
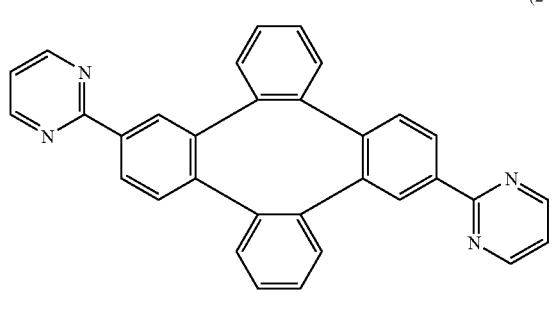
(2-16)
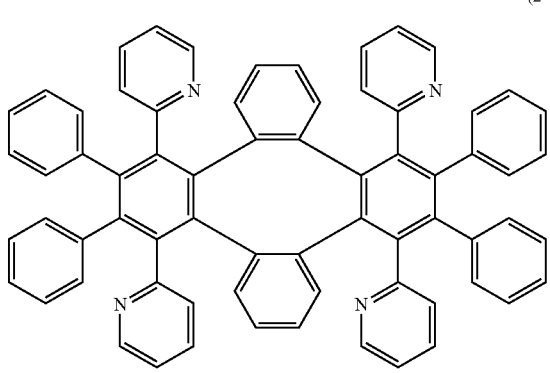
(2-17)
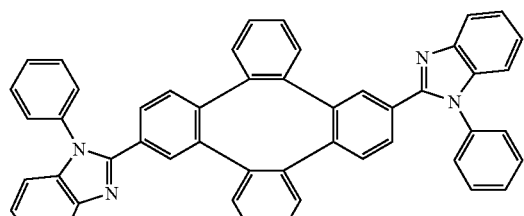
(2-18)
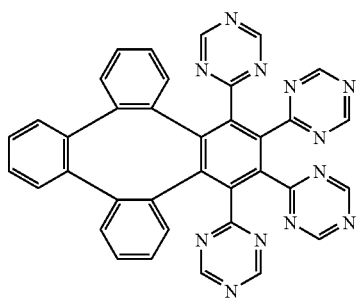
(2-19)
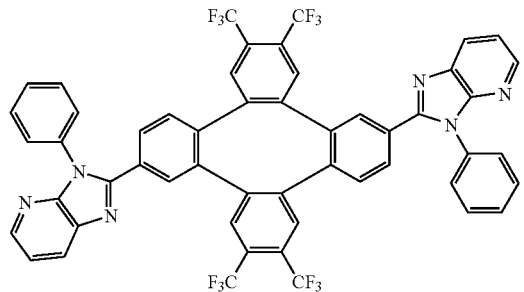
(2-20)
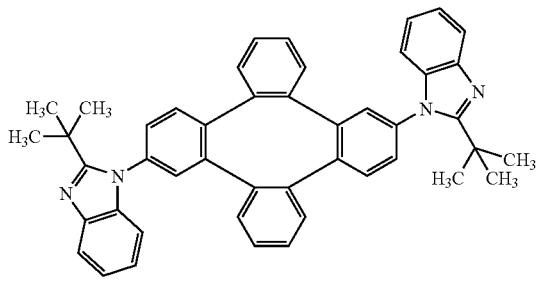

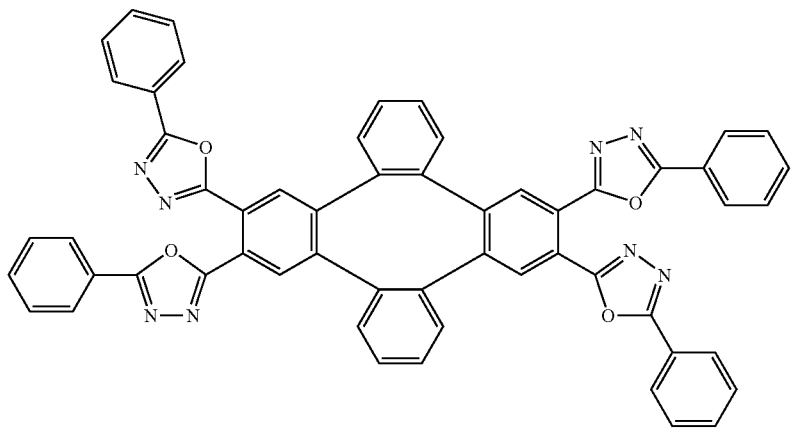
(2-21)
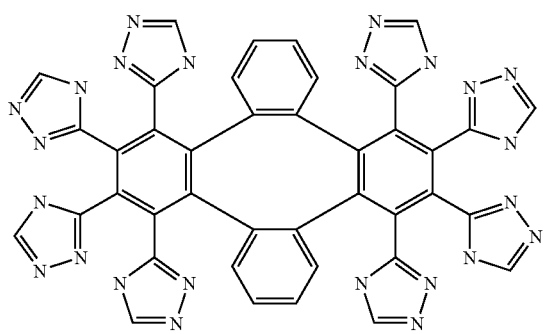
(2-22)
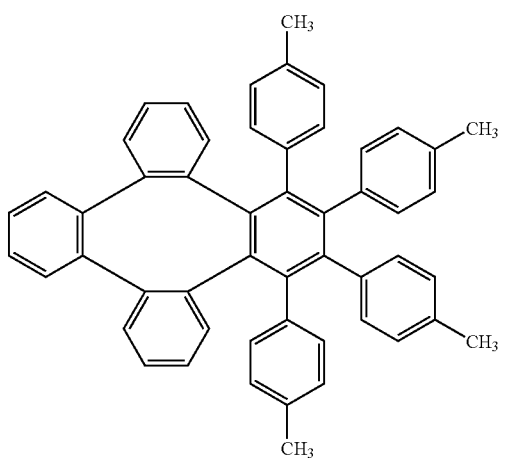
(3-1)
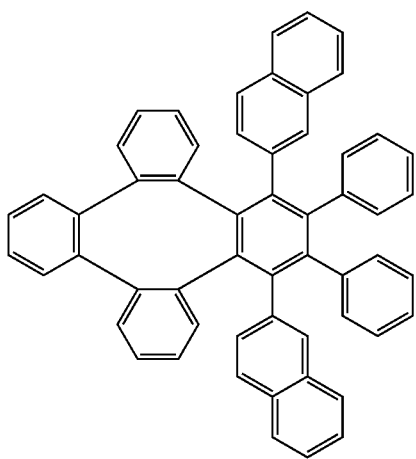
(3-2)
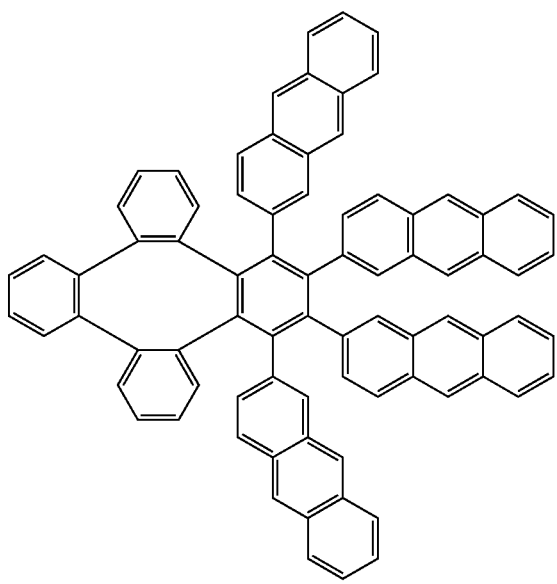
(3-3)

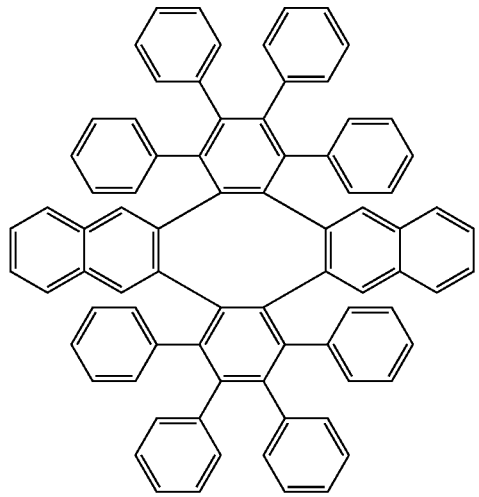
(3-4)
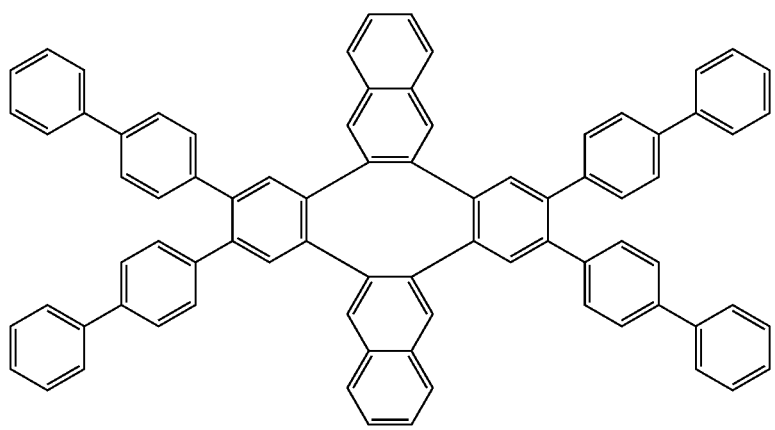
(3-5)
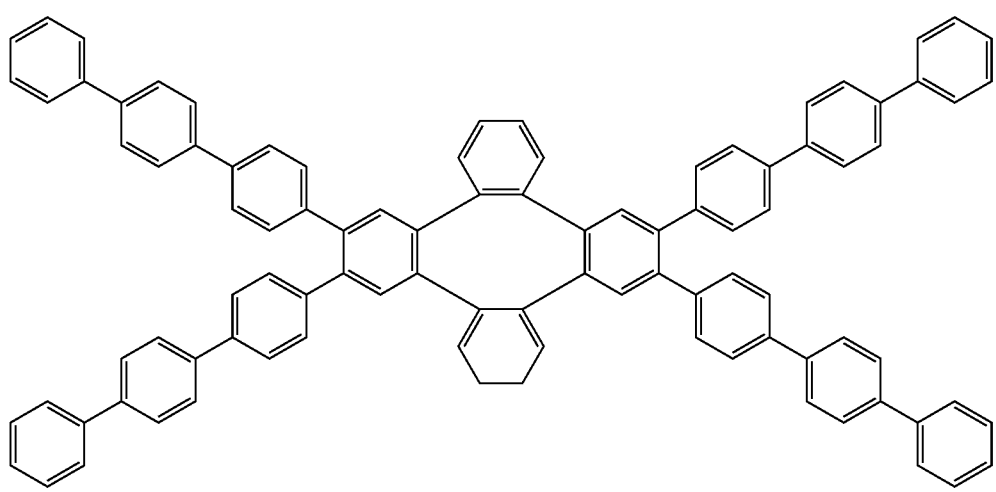
(3-6)

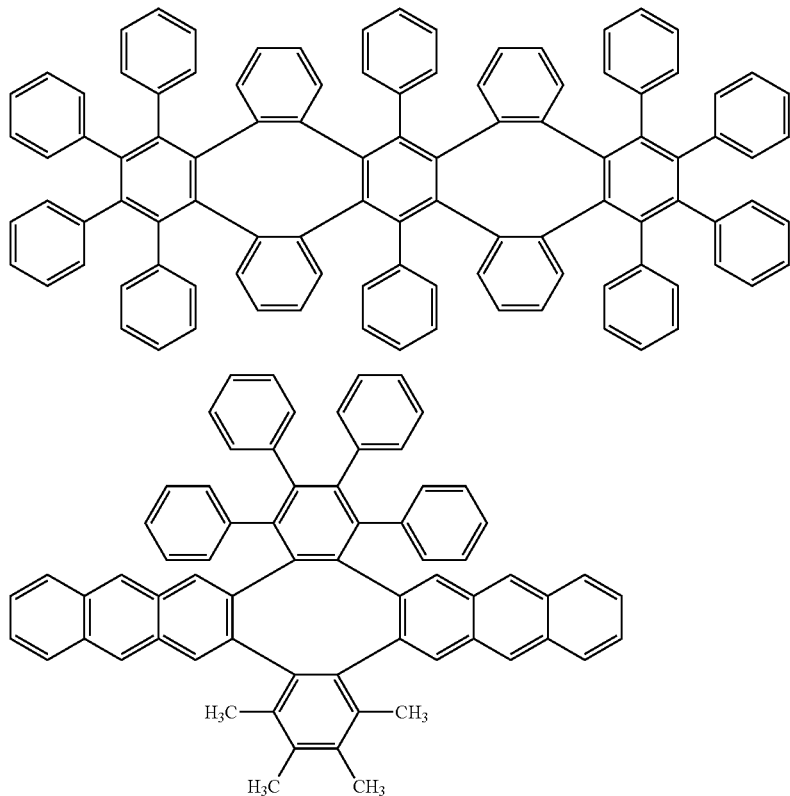

(3-7)

(3-8)

The following describes a method for producing the compound according to the present invention. The tetraphenylene skeleton contained in the compound according to the present invention can be synthesized, according to methods described in, e.g., the following documents 1 to 4.

Documents
1. Justus Liebigs Annalen der Chemie, 704, 91 (1967)
2. Tetrahedron Letters, 39, 5393 (1998)
3. Journal of Chemical Society: Perkin Transactions, 1, 159 (2001).
4. Angewandte Chemie, International Edition in English, 36, 1607 (1997)

The compounds represented by formula (1), (2), (1A), (1B) or (1C) can be synthesized by use of various known reactions for forming an aromatic carbon-carbon bond or reactions for forming a carbon-nitrogen bond. For example, the compounds can be synthesized via a reaction between a halogen compound having a tetraphenylene skeleton and a boric acid derivative, or between a halogen compound having a tetraphenylene skeleton and an aromatic amine compound in the presence of a palladium catalyst.

The halogen atom of the halogen compound, which has a tetraphenylene skeleton, is preferably a chlorine, bromine or iodine atom, particularly preferably a bromine atom.

The palladium catalyst is not particularly limited. Examples thereof include palladium tetrakistriphenylphosphine, palladium carbon, palladium acetate, and palladium dichloride (dppf), in which dppf is 1,1'-bisdiphenylphosphinoferrocene. A ligand, such as triphenylphosphine or P(t-Bu)$_3$, may be simultaneously added to the reaction system.

For the present reaction, the use of a base is preferable. The kind of the base to be used is not especially limited. Examples thereof include sodium carbonate, sodium acetate, potassium carbonate, and triethylamine. The amount of the base to be used is not particularly limited, but it is preferably from 0.1 to 20 equivalents, particularly preferably from 1 to 10 equivalents, per reaction site.

It is preferable for the present reaction to use a solvent. The solvent to be used is not particularly limited, and it may be, for example, ethanol, water, ethylene glycol dimethyl ether, diethylene glycol dimethyl ether, dimethylformamide, toluene, tetrahydrofuran, or any mixed solvent thereof.

The reaction temperature when the compound according to the present invention is synthesized is not particularly limited, and it is generally from 20 to 220° C., preferably from 20 to 180° C., more preferably from 20 to 150° C.

The compound represented by formula (1), (2), (1A), (1B) or (1C) may be contained in any layer of the luminescent device of the present invention. The compound is preferably contained in a hole-transporting layer or a light-emitting layer, and is more preferably contained in the light-emitting layer.

In the case that the light-emitting layer of the luminescent device of the present invention contains the compound represented by formula (1), (2), (1A), (1B) or (1C), the layer may contain a compound (B) for injecting/transporting electrons, together with the above-mentioned compound.

The compound for injecting/transporting electrons which can be contained in the light-emitting layer, means a compound which acts to conduct injection and/or transport of electrons into/in the light-emitting layer, and is a compound for accelerating the injection or transport of electrons by the incorporation of said compound into the light-emitting layer, or is a compound the Ea value (electron affinity) of which is a value suitable for electron injection/transport (for example, a value in the range described below).

In the case that the compound which acts to conduct injection/transport of electrons is contained in the light-emitting layer, electrons are easily injected into the light-emitting layer, thereby the driving voltage of the resultant luminescence device can be lowered. In this way, it is possible to suppress decomposition of the material resulting from a high electric field to be applied. Further, since the compound (B) plays a role to transport electrons, it is also possible to suppress decomposition of the materials resulting from injection of electrons into the compound represented by formula (1), (2), (1A), (1B) or (1C).

The Ea value (electron affinity) of the compound for injecting/transporting electrons is preferably from 2.0 to 3.5 eV, more preferably from 2.3 to 3.4 eV, even more preferably from 2.5 to 3.3 eV.

The concentration of the compound for injecting/transporting electrons in the light-emitting layer is preferably from 5 to 90% by mass, more preferably from 10 to 85% by mass, even more preferably from 10 to 80% by mass, especially preferably from 10 to 75% by mass.

When the light-emitting layer contains the compound (B) that plays a role for injection/transport of electrons, together with the compound represented by formula (1), (2), (1A), (1B) or (1C), the concentrations in the light-emitting layer of the compound represented by formula (1), (2), (1A), (1B) or (1C) and the compound (B) that can inject/transport electrons are preferably from 95 to 10% by mass and from 5 to 90% by mass, respectively, more preferably the former from 90 to 15% by mass and the latter from 10 to 85% by mass, respectively, even more preferably the former from 90 to 20% by mass and the latter from 10 to 80% by mass, respectively.

The compound for injecting/transporting electrons is preferably a metal complex (e.g. an aluminum complex, and zinc complex, but any complex having, as a ligand, a 8-hydroxyquinolinol derivative such as 2-methyl-8-hydroxyquinolinol is not preferable), a nitrogen-containing heterocyclic compound (e.g. an azole derivative, a pyridine derivative, and a triazine derivative), or an organosilicon compound (e.g. a silole derivative). The compound is more preferably a heterocyclic compound containing at least two nitrogen atoms, or a metal complex, even more preferably a heterocyclic compound containing at least two nitrogen atoms. A compound represented by the following formula (3) is particularly preferable. It is also preferable to use the following: compounds described in JP-A-2002-100476 and represented by any of formulae (A-III), (A-IV), (A-V), (A), (A-a), (A-b), (A-c), (B-II), (B-III), (B-IV), (B-V), (B-VI), (B-VII), (B-VIII), and (B-IX); and compounds described in JP-A-2000-302754 and represented by any of formulae (1) to (4) (preferable scopes thereof are as described in JP-A-2002-100476 and JP-A-2000-302754).

Formula (3)

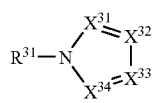

The compound represented by formula (3) is described hereinafter. $R^{31}$ represents a hydrogen atom or a substituent. The substituent may be the same as described above. $R^{31}$ is preferably an alkyl, aryl, or heteroaryl group, more preferably an aryl or heteroaryl group, further preferably an aryl group.

Herein, in the present specification and claims, the wording "heteroaryl group" means a group in which at least one of the carbon atoms that constitute an aryl group is substituted with an atom selected from N, O and S.

$X^{31}$, $X^{32}$, $X^{33}$ and $X^{34}$ each independently represent a nitrogen atom, or a substituted or unsubstituted carbon atom. At least one of $X^{31}$, $X^{32}$, $X^{33}$ and $X^{34}$ is a nitrogen atom. The substituent on the carbon atom may be the same group as described on the above-mentioned $R^{31}$, and is preferably an alkyl, aryl, or heteroaryl group.

It is preferable that $X^{31}$ is a substituted or unsubstituted carbon atom, $X^{32}$ is a nitrogen atom, and $X^{33}$ and $X^{34}$ each are a substituted carbon atom. It is also preferable that the substituents on $X^{33}$ and $X^{34}$ bond together, to form an aromatic ring.

The compound represented by formula (3) is preferably a compound represented by the following formula (4) or (5), more preferably a compound represented by formula (4).

Formula (4)

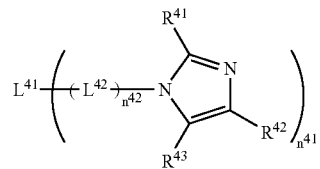

Formula (5)

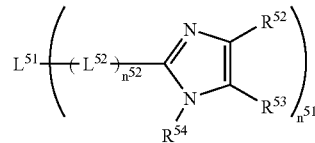

The following describes the compound of the formula (4). $R^{41}$, $R^{42}$ and $R^{43}$ each independently represent a hydrogen atom or a substituent. The substituent may be, for example, the same group as described on the above-mentioned $R^{31}$.

$R^{41}$ is preferably an alkyl, aryl or heteroaryl group, more preferably an alkyl or aryl group, even more preferably an alkyl group.

$R^{42}$ and $R^{43}$ are each preferably an alkyl, aryl, or heteroaryl group, or are preferably bond together to form an aromatic group. $R^{42}$ and $R^{43}$ are more preferably groups that bond together, to form an aromatic group.

$L^{41}$ represents a linking group. The linking group may be a polymer main chain, such as polyalkylene or polyester. The linking group may form, for example, a polyvinyl imidazole derivative. $L^{41}$ is preferably an aryl linking group, a heteroaryl linking group, an alkyl linking group, or an alkylene polymer main chain, more preferably an aryl linking group, or a heteroaryl linking group, even more preferably a nitrogen-containing heteroaryl linking group.

$n^{41}$ represents an integer of 2 or more. The nitrogen-containing heterocyclic groups connected to $L^{41}$ may be the same or different. In the case that $L^{41}$ is not any polymer main chain, $n^{41}$ is preferably from 2 to 6, more preferably 3 or 4. In the case that the $L^{41}$ is a polymer main chain, $n^{41}$ would be a value corresponding to the number of recurring units of the polymer main chain (for example, in the case of a 100-mer of vinylcarbazole, $n^{41}$ is 100).

$L^{42}$ represents a divalent linking group. $L^{42}$ is preferably an alkylene group, an arylene group, a heteroarylene group, an oxygen linking group, a carbonyl linking group, or an amino linking group, more preferably an alkylene group, or an arylene group.

$n^{42}$ represents an integer of 0 to 6, preferably from 0 to 3, more preferably 0 or 1. In the case that $n^{42}$ is 2 or more, $L^{42}$s may be the same or different.

The following describes the compound of the formula (5). $R^{52}$ and $R^{53}$ each independently represent a hydrogen atom or a substituent. The substituent may be, for example, the same group as described on the above-mentioned $R^{31}$.

$R^{52}$ and $R^{53}$ are each preferably an alkyl, aryl, or heteroaryl group, or are preferably groups bonded to each other to form an aromatic group. $R^{52}$ and $R^{53}$ are more preferably groups that bond together to form an aromatic group, even more preferably groups that bond together to form a nitrogen-containing aromatic group.

$R^{54}$ represents a hydrogen atom or a substituent. The substituent may be, for example, the same group as described on the above-mentioned $R^{31}$ (or $R^{11}$). $R^{54}$ is preferably an alkyl, aryl or heteroaryl group, more preferably an aryl or heteroaryl group, even more preferably an aryl group.

$L^{51}$, $L^{52}$, $n^{51}$ and $n^{52}$ have the same meanings as the above $L^{41}$, $L^{42}$, $n^{41}$ and $n^{42}$, respectively, and the preferable scopes thereof are also the same.

The luminescent device of the present invention is described below. The luminescent device of the present invention is not particularly limited as to the system, driving method, and utilizing form, as long as the device utilizes the aforesaid compound according to the present invention. Those luminescent devices which contain the compound according to the present invention and the phosphorescent material in the same layer, are preferred. Typical luminescent devices include organic EL (electroluminescence) devices.

In the present invention, the organic layer means to include a hole transporting layer, a light-emitting layer, and other layers.

Method for forming the organic layer of the luminescent device containing the compound according to the present invention is not particularly limited, and use may be made of any of a resistance heating deposition method, an electron beam method, a sputtering method, a molecular layer-accumulating method, a coating method, an ink jet method, a printing method, and a transfer method, with the resistance heating deposition method, the coating method and the transfer method being preferred in view of performance and production.

The luminescent device of the present invention is a device, in which at least one organic-compound layer including a light-emitting layer (which may include the case of a sole light-emitting layer), is formed between a pair of electrodes of an anode and a cathode. The luminescent device may have not only the light-emitting layer but also any of a hole injecting layer, a hole transporting layer, an electron injecting layer, an electron transporting layer, a protective layer, and the like. Each of these layers may have some other function. In order to form each of the layers, various materials may be used.

The anode functions to feed holes to the hole injecting layer, the hole transporting layer, and the light-emitting layer. A metal, an alloy, a metal oxide, an electroconductive compound, or a mixture thereof may be used for the anode, with a material having a work function of 4 eV or more being preferred. Specific examples of the material of the anode include conductive metal oxides, e.g. tin oxide, zinc oxide, indium oxide, and indium tin oxide (ITO); metals, e.g. gold, silver, chromium, and nickel; mixtures or layered products of the metal and the conductive metal oxide; inorganic conductive substances, e.g. copper iodide, and copper sulfide; organic conductive materials, e.g. polyaniline, polythiophene, and polypyrrole; and layered products of any of these and ITO, with conductive metal oxides being preferred. In particular, in view of productivity, high conductivity and transparency, ITO is preferred. The film thickness of the anode may properly be selected depending upon the kind of the material, but it is preferably 10 nm to 5 µm, more preferably 50 nm to 1 µm, still more preferably 100 nm to 500 nm.

As the anode, generally, those which are formed as a layer on, for example, soda-lime glass, alkali-free glass, or a transparent resin substrate, can be used. In the case of using glass, alkali-free glass is preferably used, in order to reduce the amount of ion released from the glass. Also, in the case of using soda-lime glass, it is preferred to provide a barrier coat, for example, of silica, on the glass. Thickness of the substrate is not particularly limited as long as a sufficient mechanical strength is obtained. In the case of using glass, glass of generally 0.2 mm or more, preferably 0.7 mm or more, in thickness, is used.

Various methods may be employed for forming the anode depending upon kind of the material to be used. In the case of, for example, ITO, the anode film is formed, by an electron beam method, a sputtering method, a resistance heating deposition method, a chemical reaction method (e.g., a sol-gel method), or a method of coating a dispersion of indium tin oxide.

The anode may be subjected to a treatment of, for example, washing, to reduce the voltage for driving the device or enhance light-emitting efficiency. In the case of, for example, ITO, UV-ozone treatment, plasma treatment, or the like is effective.

The cathode functions to feed electrons to the electron injecting layer, the electron transporting layer, and the light-emitting layer. The material of the cathode can be selected, taking into consideration, for example, adhesion to such a layer adjacent to the cathode (negative electrode) as the electron injecting layer, the electron transporting layer or the light-emitting layer, ionization potential, and stability. Examples of the material that can be used for the cathode, include a metal, an alloy, a metal halide, a metal oxide, an electroconductive compound, or a mixture thereof. Specific examples include an alkali metal (e.g., Li, Na or K), and the fluoride or oxide thereof; an alkaline earth metal (e.g., Mg or Ca), and the fluoride or oxide thereof; gold, silver, lead, aluminum, a sodium-potassium alloy or a mixed metal thereof; a lithium-aluminum alloy or a mixed metal thereof; a magnesium-silver alloy or a mixed metal thereof; and a rare earth metal, e.g. indium or ytterbium. The cathode material is preferably a material having a work function of 4 eV or less, more preferably aluminum, a lithium-aluminum alloy or a mixed metal thereof, a magnesium-silver alloy or a mixed metal thereof, or the like. The cathode may be of a single-layered structure of the above-described compound or the mixture, or of a multi-layered structure containing the above-described compound or the mixture. For example, a layered structure of aluminum/lithium fluoride or aluminum/lithium oxide is preferred. The film thickness of the cathode may properly be selected depending upon the kind of the material, but is preferably 10 nm to 5 µm, more preferably 50 nm to 1 µm, still more preferably 100 nm to 1 µm.

For forming the cathode, there may be employed a method, e.g. an electron beam method, a sputtering method, a resistance heating deposition method, or a coating method. It is possible to deposit a single metal or to deposit two or more components simultaneously. Further, a plurality of metals may simultaneously be deposited to form an alloy electrode, or a previously provided alloy may be deposited.

As to sheet resistance of the anode and the cathode, the lower, the better. A sheet resistance of several hundreds Ω/□ (Ω/quadrature or Ω/square) or less is preferred.

As the material for the light-emitting layer, any of those may be used which can form a layer that, when an electric field is applied thereto, permits injection of holes from the anode, the hole injecting layer or the hole transporting layer and injection of electrons from the cathode, the electron injecting layer or the electron transporting layer; that functions to migrate injected charges; and that provides a site for recombination of the hole and the electron, to emit light. Examples of the light-emitting layer material, include various metal complexes represented by rare earth complexes or metal complexes of 8-quinolinol, benzoxazole, benzimidazole, benzothiazole, styrylbenzene, polyphenyl, diphenylbutadiene, tetraphenylbutadiene, naphthalimide, coumarin, perylene, perynone, oxadiazole, aldazine, pyralidine, cyclopentadiene, bis-styrylanthracene, quinacridone, pyrrolopyridine, thiadiazolopyridine, cyclopentadiene, styrylamine, aromatic dimethylidene compound; polymer compounds, e.g. polythiophene, polyphenylene, and polyphenylene vinylene; organosilicons, iridium-tris-phenylpyridine complex, transition metal complexes represented by platinum-porphyrin complex, and the derivatives thereof. At least one material for the light-emitting layer is a phosphorescent material. Thickness of the light-emitting layer is not particularly limited, but is preferably 1 nm to 5 μm, more preferably 5 nm to 1 μm, still more preferably 10 nm to 500 nm.

Method for forming the light-emitting layer is not particularly limited, and use may be made of any of a resistance heating deposition method, an electron beam method, a sputtering method, a molecular layer-accumulating method, a coating method (e.g. a spin coating method, a cast method, and a dip coating method), an ink jet method, a printing method, an LB method, and a transfer method, with the resistance heating deposition method and the coating method being preferred.

The light-emitting layer may be formed from a single compound or a plurality of compounds. Also, the number of light-emitting layers may be one, or two or more. A plurality of the light-emitting layers may emit lights of different colors, to thereby emit, for example, a white light. A white light may be emitted from a single light-emitting layer. When a plurality of the light-emitting layers are formed, each light-emitting layer may be formed from a single material or a plurality of compounds.

As the materials for the hole injecting layer and the hole transporting layer, those materials may be used which have any one of the function of injecting holes from the anode side, the function of transporting holes, and the function of blocking electrons injected from the cathode. Specific examples thereof include a conductive high molecular oligomer, e.g. polythiophene, a thiophene oligomer, an aniline-series copolymer, poly(N-vinylcarbazole), polysilane-series compounds, porphyrin-series compounds, aromatic dimethylidene-series compounds, stilylamine compounds, aromatic tertiary amine compounds, carbazole, triazole, oxazole, oxadiazole, imidazole, polyarylalkane, pyrazoline, pyrazolone, phenylenediamine, arylamine, amino-substituted chalcone, styrylanthracene, fluorenone, hydrazone, stilbene, silazane, organic silane derivatives, carbon films, the compounds according to the present invention, and the derivatives thereof. Thickness of the hole injecting layer and the hole transporting layer is not particularly limited, but is preferably 1 nm to 5 μm, more preferably 5 nm to 1 μm, still more preferably 10 nm to 500 nm. The hole injecting layer and the hole transporting layer may be of a single layer structure composed of one or more of the above-described materials, or may be of a multi-layer structure composed of a plurality of layers having the same composition or different compositions.

Method for forming the hole injecting layer or the hole transporting layer is not particularly limited, and use can be made of any of a vacuum deposition method, an LB method, a coating method of dissolving or dispersing the aforesaid hole injecting/transporting material in a solvent (e.g., a spin coating method, a cast coating method or a dip coating method), an ink jet method, a printing method, and a transfer method. In the coating method, the material may be dissolved or dispersed together with a resin component. As the resin component, there are illustrated, for example, poly(vinyl chloride), polycarbonate, polystyrene, poly(methyl methacrylate), poly(butyl methacrylate), polyester, polysulfone, poly(phenylene oxide), polybutadiene, poly(N-vinylcarbazole), hydrocarbon resin, ketone resin, phenoxy resin, polyamide, ethyl cellulose, vinyl acetate, ABS resin, polyurethane, melamine resin, unsaturated polyester resin, alkyd resin, epoxy resin, and silicone resin.

As the materials for the electron injecting layer and the electron transporting layer, those materials may be used which have any one of the function of injecting electrons from the cathode side, the function of transporting electrons, and the function of blocking holes injected from the anode. Specific examples thereof include various metal complexes represented by metal complexes having, as a ligand, benzothiazole or benzoxazole, metal phthalocyanine or metal complex of 8-quinolinol, phthalocyanine, tetracarboxylic acid anhydride of an aromatic compound such as perylene, naphthalene, triazole, oxazole, oxadiazole, imidazole, fluorenone, anthraquinodimethane, anthrone, diphenylquinone, thiopyran dioxide, carbodiimide, fluorenylidenemethane, distyrylpyrazine, organic silane, the compound according to the present invention, and the derivatives thereof. Thickness of the electron injecting layer and the electron transporting layer is not particularly limited, but is preferably 1 nm to 5 μm, more preferably 5 nm to 1 μm, still more preferably 10 nm to 500 nm. The electron injecting layer and the electron transporting layer may be of a single layer structure composed of one or more of the above-described materials, or may be of a multi-layer structure composed of a plurality of layers having the same composition or different compositions.

A method for forming the electron injecting layer and the electron transporting layer is not particularly limited, and use can be made of any of a vacuum deposition method, an LB method, a coating method of dissolving or dispersing the aforesaid electron injecting/transporting material in a solvent (e.g., a spin coating method, a casting method or a dip coating method), an ink jet method, a printing method, and a transfer method. In the coating method, the material may be dissolved or dispersed together with a resin component, and, as the resin component, there may be used, for example, those which have been illustrated with respect to the hole injecting/transporting layer.

As materials for the protective layer, any material may be used that can prevent invasion of substances capable of accelerating deterioration of the luminescent device, such as moisture or oxygen, into the device. Specific examples thereof include metals, e.g. In, Sn, Pb, Au, Cu, Ag, Al, Ti, and Ni; metal oxides, e.g. MgO, SiO, $SiO_2$, $Al_2O_3$, GeO, NiO, CaO, BaO, $Fe_2O_3$, $Y_2O_3$, and $TiO_2$; metal fluorides, e.g. $MgF_2$, LiF, $AlF_3$, and $CaF_2$; nitrides, e.g. $SiN_x$, and $SiO_xN_y$; polyethylene, polypropylene, poly(methyl methacrylate), polyimide, polyurea, polytetrafluoroethylene, polychlorotrifluoroethylene, polydichlorodifluoroethylene, a copolymer of chlorotrifluoroethylene and dichlorodifluoroethylene, a copolymer obtained by copolymerizing a monomer mixture containing at least one comonomer and tetrafluoroethylene, a fluorine-containing copolymer having a cyclic structure in the main chain of the copolymer, a water-absorbing substance showing a water absorption of 1% or more, and a moisture barrier substance showing a water absorption of less than 0.1%.

A method for forming the protective layer is not particularly limited, and use may be made, for example, of a vacuum deposition method, a sputtering method, a reactive sputtering method, an MBE (molecular beam epitaxy) method, a cluster ion beam method, an ion plating method, a plasma polymerization method (high frequency-excited ion plating method), a plasma CVD (chemical vapor deposition) method, a laser CVD method, a heat CVD method, a gas source CVD method, a coating method, a printing method, or a transfer method.

The luminescence device (the organic electroluminescence device) of the present invention is excellent in luminescence property and durability, in particular long-term driving durability (drivability), and the like.

The compound of the present invention is preferable to be utilized, for example, in an organic electroluminescence device excellent in luminescence property and driving durability (in particular, long-term drivability).

The present invention will be described in more detail based on the following examples, but the invention is not intended to be limited thereto.

EXAMPLES

Example 1

A washed ITO substrate was placed in a depositing apparatus. As a hole transporting material, α-NPD (N,N'-diphenyl-N,N'-di(α-naphthyl)benzidine) was deposited in a thickness of 50 nm on the substrate, then Compound (1-4) and Compound a were co-deposited thereon with a ratio (by mass) of 17:1 in a thickness of 36 nm, followed by depositing Azole compound b thereon in a thickness of 36 nm. A patterned mask (mask providing a light-emitting area of 4 mm×5 mm) was provided on the organic thin layers, and after depositing lithium fluoride in a thickness of about 1 nm in the depositing apparatus, aluminum was deposited in a thickness of about 200 nm thereon, to prepare a luminescent device. A DC constant voltage was applied to the resultant EL device, using Source Measure Unit type 2400 (trade name), manufactured by Toyo Tekunika, to emit light. The luminance of the thus-emitted light was measured, using a luminance meter, BM-8 (trade name) manufactured by Topkon, and the wavelength of the emitted light was measured, using a spectrum analyzer, PMA-11 (trade name) manufactured by Hamamatsu Photonics.

As a result, a green light emission with a chromaticity value of (0.27, 0.62) was obtained. The external quantum efficiency of the device calculated in a usual manner was 7.1%.

The device durability of this device was evaluated at an initial luminance of 2,000 $cd/m^2$ and a constant current value. As a result, the luminance half time of the device was about 520 hours.

The structures of compounds used in this example and the following examples are illustrated below.

Compound a

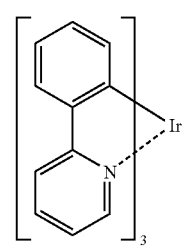

Azole compound b

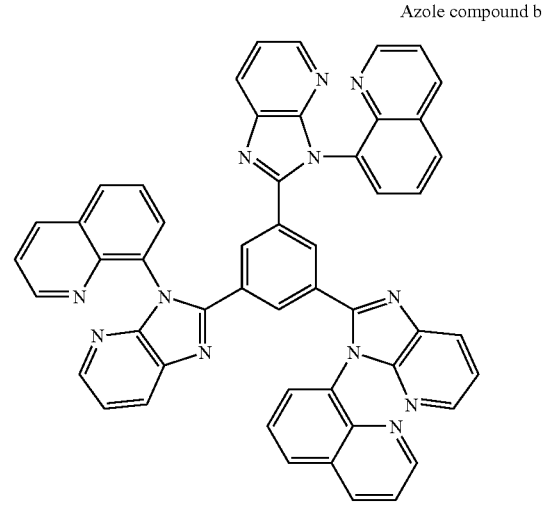

CBP

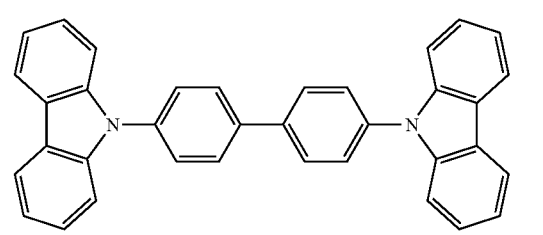

Compound c

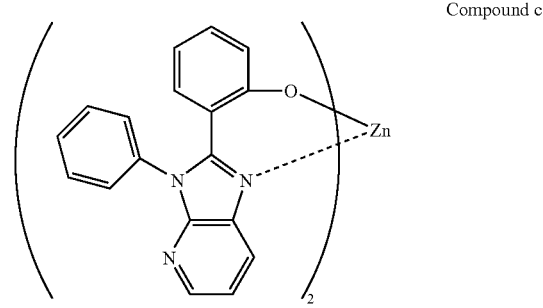

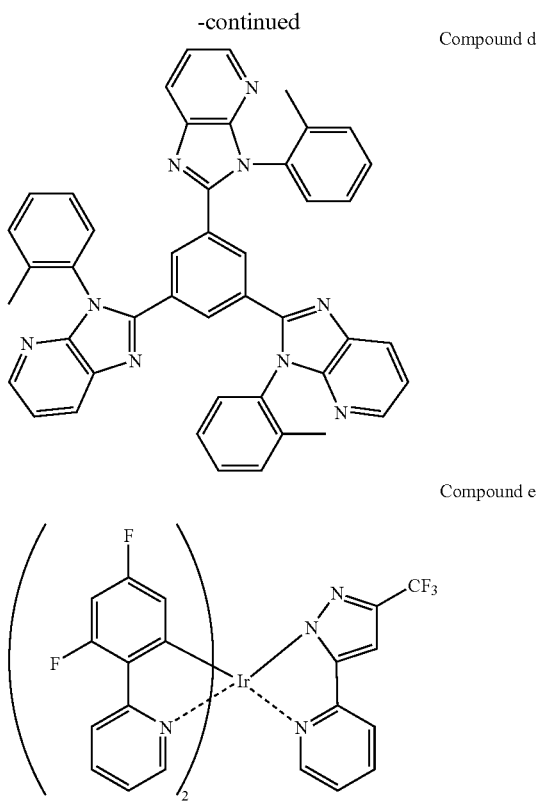

Compound d

Compound e

Example 2

A device was prepared and evaluated in the same manner as in Example 1, except that instead of the Compound (1-4), a mixture of Compound (1-4) and Compound c at a ratio by mass of 1:1 was used. As a result, a green light emission with a chromaticity value of (0.28, 0.62) was obtained. The external quantum efficiency of the device was 12.1%.

The device durability of this device was evaluated at an initial luminance of 2,000 cd/m$^2$ and a constant current value. As a result, the luminance half time of the device was about 620 hours.

Example 3

A device was prepared and evaluated in the same manner as in Example 1, except that instead of the Compound (1-4), a mixture of Compound (1-4) and Compound d at a ratio by mass of 1:1 was used. As a result, a green light emission with a chromaticity value of (0.28, 0.62) was obtained. The external quantum efficiency of the device was 9.1%.

The device durability of this device was evaluated at an initial luminance of 2,000 cd/m$^2$ and a constant current value. As a result, the luminance half time of the device was about 780 hours.

Example 4

A device was prepared and evaluated in the same manner as in Example 1, except that instead of the Compound a, Compound e was used. As a result, a blue light emission with a chromaticity value of (0.17, 0.26) was obtained. The external quantum efficiency of the device was 9.5%.

The device durability of this device was evaluated at an initial luminance of 2,000 cd/m$^2$ and a constant current value. As a result, the luminance half time of the device was about 400 hours.

Example 5

A device was prepared and evaluated in the same manner as in Example 1, except that Compound (1-5) was used instead of the α-NPD and CBP (4,4'-bis(N-carbazolyl)biphenyl) was used instead of the Compound (1-4). As a result, a green light emission with a chromaticity value of (0.27, 0.61) was obtained. The external quantum efficiency of the device was 13.2%.

The device durability of this device was evaluated at an initial luminance of 2,000 cd/m$^2$ and a constant current value. As a result, the luminance half time of the device was about 280 hours.

Example 6

A washed ITO glass substrate was spin-coated with Baytron P (a solution of PEDOT-PSS (polyethylenedioxythiophene doped with polystyrenesulfonic acid), trade name, manufactured by Bayer) for a hole transporting layer, and then the resultant substrate was vacuum-dried at 100° C. for 1 hour (to form a film of about 100 nm thickness). Into 3.8 g of chloroform, were dissolved 40 mg of Polymer (1-11), 1 mg of Compound a and 6 mg of Compound d, and then with the resultant solution, the above-mentioned substrate was spin-coated (film thickness: about 50 to 70 nm). The resultant substrate was vacuum-dried at 100° C. for 30 minutes. On the substrate, the electron transporting material d and LiF were vapor-deposited, in this order, such that the film thickness thereof would be about 36 nm and about 1 nm, respectively, under the conditions at a substrate temperature of room temperature, in a vacuum at $10^{-3}$ to $10^{-4}$ Pa. Thereon was set a patterned mask (having a luminescence area of 5 nm×4 nm). Aluminum was vapor-deposited thereon so as to have a film thickness of about 200 nm. Thus, a device was prepared.

A DC constant voltage was applied to the resultant device, using Source Measure Unit type 2400, manufactured by Toyo Tekunika, to emit light. The luminance of the thus-emitted light was measured, using a luminance meter, BM-8 (trade name) manufactured by Topkon, and the wavelength of the emitted light was measured, using a spectrum analyzer, PMA-11 (trade name) manufactured by Hamamatsu Photonics.

As a result, a green light emission with a chromaticity value of (0.26, 0.60) was obtained. The external quantum efficiency of the device was 7.1%.

The device durability of this device was evaluated at an initial luminance of 2,000 cd/m$^2$ and a constant current value. As a result, the luminance half time of the device was about 120 hours.

Similarly, by using the compounds according to the present invention other than the above, high-efficiency luminescent devices can be produced.

Having described our invention as related to the present embodiments, it is our intention that the invention not be limited by any of the details of the description, unless otherwise specified, but rather be construed broadly within its spirit and scope as set out in the accompanying claims.

What is claimed is:

1. An organic electroluminescent device, having, between a pair of electrodes, at least one organic layer including a light-emitting layer, wherein the organic layer contains at least one compound represented by formula (1), and wherein the light-emitting layer contains a phosphorescent material:

Formula (1)

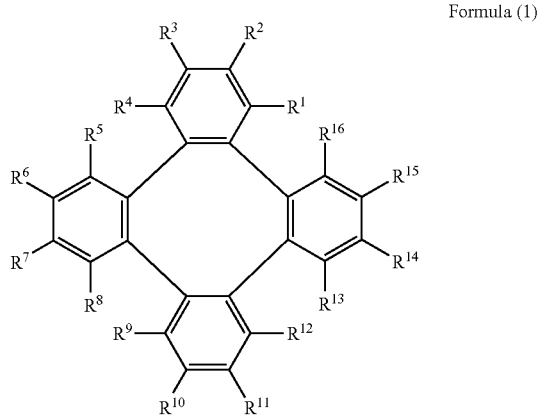

wherein, in formula (1), $R^1, R^2, R^3, R^4, R^5, R^6, R^7, R^8, R^9, R^{10}, R^{11}, R^{12}, R^{13}, R^{14}, R^{15}$, and $R^{16}$ each represent a hydrogen atom or a substituent, and at least one of $R^1$ to $R^{16}$ represents a heteroaryl group.

2. The organic electroluminescent device of claim 1, wherein the compound represented by formula (1) is contained in the light-emitting layer.

3. The organic electroluminescent device of claim 1, wherein the light-emitting layer contains an electron-injecting/transporting compound.

4. The organic electroluminescent device of claim 3, wherein the electron-injecting/transporting compound is a metal complex.

5. The organic electroluminescent device of claim 3, wherein the electron-injecting/transporting compound is a heterocyclic compound containing at least two nitrogen atoms.

6. The organic electroluminescent device of claim 1, wherein said substituent is selected from the group consisting of $C_{1-30}$ alkyl, $C_{2-30}$ alkenyl, $C_{2-30}$ alkynyl, $C_{6-30}$ aryl, an amino group having 0 to 30 carbon atoms, an alkoxy group having 1 to 30 carbon atoms, an aryloxy group having 6 to 30 carbon atoms, a heteroaryl oxy group having 1 to 30 carbon atoms, an acyl group having 1 to 30 carbon atoms, an alkoxycarbonyl group having 2 to 30 carbon atoms, an aryloxycarbonyl group having 7 to 30 carbon atoms, an acyloxy group having 2 to 30 carbon atoms, an acylamino group having 2 to 30 carbon atoms, an alkoxycarbonylamino group having 2 to 30 carbon atoms, group having 0 to 30 carbon atoms, a carbamoyl group having 1 to 30 carbon atoms, an alkylthio group having 1 to 30 carbon atoms, an arylthio group having 6 to 30 carbon atoms, a heteroaryl thio group having 1 to 30 carbon atoms, a sulfonyl group having 1 to 30 carbon atoms, a sulfinyl group having 1 to 30 carbon atoms, a ureido group having 1 to 30 carbon atoms, a phosphoric acid amido group having 1 to 30 carbon atoms, a hydroxyl group, a mercapto group, a halogen atom, a cyano group, a sulfo group, a carboxyl group, a nitro group, a hydroxamic acid group, a sulfino group, a hydrazino group, an imino group, a heterocyclic group having 1 to 30 carbon atoms with a hetero atom, and a silyl group having 3 to 40 carbon atoms.

7. An organic electroluminescent device, having, between a pair of electrodes, at least one organic layer including a light-emitting layer containing a phosphorescent material, wherein the organic layer contains at least one compound represented by formula (2):

$L\text{-}(T)_n$  Formula (2)

wherein, in formula (2), L represents a divalent or higher valent aromatic hetero ring; T represents a group obtained by removing an atom from any one of $R^1$ to $R^{16}$ in a structure represented by formula (1), or a group obtained by removing any one of $R^1$ to $R^{16}$ from a compound represented by formula (1); T's may be the same or different from each other; and n represents an integer of 2 or more;

Formula (1)

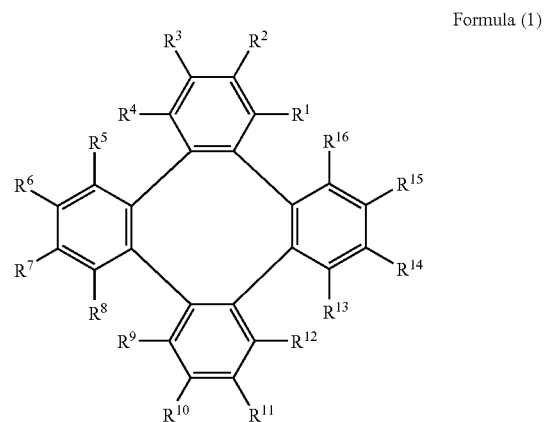

wherein, in formula (1), $R^1, R^2, R^3, R^4, R^5, R^6, R^7, R^8, R^9, R^{10}, R^{11}, R^{12}, R^{13}, R^{14}, R^{15}$, and $R^{16}$ each represent a hydrogen atom or a substituent.

8. The organic electroluminescent device of claim 7, wherein the compound represented by formula (2) is contained in the light-emitting layer.

9. The organic electroluminescent device of claim 7, wherein the light-emitting layer contains an electron-injecting/transporting compound.

10. The organic electroluminescent device of claim 9, wherein the electron-injecting/transporting compound is a metal complex.

11. The organic electroluminescent device of claim 9, wherein the electron-injecting/transporting compound is a heterocyclic compound containing at least two nitrogen atoms.

12. The organic electroluminescent device of claim 7, wherein said substituent is selected from the group consisting of $C_{1-30}$ alkyl, $C_{2-30}$ alkenyl, $C_{2-30}$ alkynyl, $C_{6-30}$ aryl, an amino group having 0 to 30 carbon atoms, an alkoxy group having 1 to 30 carbon atoms, an aryloxy group having 6 to 30 carbon atoms, a heteroaryl oxy group having 1 to 30 carbon atoms, an acyl group having 1 to 30 carbon atoms, an alkoxycarbonyl group having 2 to 30 carbon atoms, an aryloxycarbonyl group having 7 to 30 carbon atoms, an acyloxy group having 2 to 30 carbon atoms, an acylamino group having 2 to 30 carbon atoms, an alkoxycarbonylamino group having 2 to 30 carbon atoms, an aryloxycarbonylamino group having 7 to 30 carbon atoms, a sulfonylamino group having 1 to 30 carbon atoms, a sulfamoyl carbon atoms, an alkoxycarbonylamino group having 2 to 30 carbon atoms, an aryloxycarbonylamino group having 7 to 30 carbon atoms, a sulfonylamino group having 1 to 30 carbon atoms, a sulfamoyl group having 0 to 30 carbon atoms, a carbamoyl group having 1 to 30 carbon atoms, an alkylthio group having 1 to 30 carbon atoms, an arylthio group having 6 to 30 carbon atoms, a heteroaryl thio group having 1 to 30 carbon atoms, a sulfonyl group having 1 to 30 carbon atoms, a sulfinyl group having 1 to 30 carbon atoms, a ureido group having 1 to 30 carbon atoms, a phosphoric acid amido group having 1 to 30 carbon atoms, a hydroxyl group, a mercapto group, a halogen atom, a cyano group, a sulfo group, a carboxyl group, a nitro group, a hydroxamic acid group, a sulfino group, a hydrazino group, an imino group, a heterocyclic group having 1 to 30 carbon atoms with a hetero atom, and a silyl group having 3 to 40 carbon atoms.

13. The organic electroluminescent device of claim 7, wherein said divalent or higher valent aromatic hetero ring is selected from the group consisting of a triazole ring, a pyridine ring, and a pyrimidine ring.

14. An organic electroluminescent device, having, between a pair of electrodes, at least one organic layer including a light-emitting layer, wherein the organic layer contains at least one compound represented by formula (1), and wherein the light-emitting layer contains a phosphorescent material:

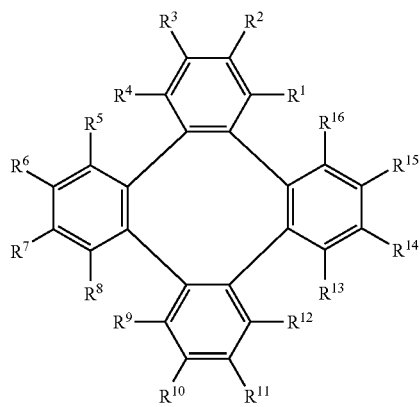

Formula (1)

wherein, in formula (1), $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ each represent a hydrogen atom or a substituent, and at least one of $R^1$ to $R^{16}$ represents a carbazolyl group.

15. The organic electroluminescent device of claim 14, wherein said substituent is selected from the group consisting of $C_{1-30}$ alkyl, $C_{2-30}$ alkenyl, $C_{2-30}$ alkynyl, $C_{6-30}$ aryl, an amino group having 0 to 30 carbon atoms, an alkoxy group having 1 to 30 carbon atoms, an aryloxy group having 6 to 30 carbon atoms, a heteroaryl oxy group having 1 to 30 carbon atoms, an acyl group having 1 to 30 carbon atoms, an alkoxycarbonyl group having 2 to 30 carbon atoms, an aryloxycarbonyl group having 7 to 30 carbon atoms, an acyloxy group having 2 to 30 carbon atoms, an acylamino group having 2 to 30 an aryloxycarbonylamino group having 7 to 30 carbon atoms, a sulfonylamino group having 1 to 30 carbon atoms, a sulfamoyl group having 0 to 30 carbon atoms, a carbamoyl group having 1 to 30 carbon atoms, an alkylthio group having 1 to 30 carbon atoms, an arylthio group having 6 to 30 carbon atoms, a heteroaryl thio group having 1 to 30 carbon atoms, a sulfonyl group having 1 to 30 carbon atoms, a sulfinyl group having 1 to 30 carbon atoms, a ureido group having 1 to 30 carbon atoms, a phosphoric acid amido group having 1 to 30 carbon atoms, a hydroxyl group, a mercapto group, a halogen atom, a cyano group, a sulfo group, a carboxyl group, a nitro group, a hydroxamic acid group, a sulfino group, a hydrazino group, an imino group, a heterocyclic group having 1 to 30 carbon atoms with a hetero atom, and a silyl group having 3 to 40 carbon atoms.

* * * * *